(12) United States Patent
Lipkens et al.

(10) Patent No.: US 9,686,096 B2
(45) Date of Patent: Jun. 20, 2017

(54) ACOUSTIC MANIPULATION OF PARTICLES IN STANDING WAVE FIELDS

(71) Applicant: FloDesign Sonics, Inc., Wilbraham, MA (US)

(72) Inventors: Bart Lipkens, Hampden, MA (US); Benjamin Ross-Johnsrud, Springfield, MA (US); Evgenia Zabolotskaya, Austin, TX (US); Yurii Ilinskii, Austin, TX (US)

(73) Assignee: FLODESIGN SONICS, INC., Wilbraham, MA (US)

( * ) Notice: Subject to any disclaimer, the term of this patent is extended or adjusted under 35 U.S.C. 154(b) by 0 days.

(21) Appl. No.: 15/414,465

(22) Filed: Jan. 24, 2017

(65) Prior Publication Data

US 2017/0128857 A1 May 11, 2017

Related U.S. Application Data

(63) Continuation-in-part of application No. 15/161,108, filed on May 20, 2016, now Pat. No. 9,550,134.

(60) Provisional application No. 62/163,994, filed on May 20, 2015.

(51) Int. Cl.
*B01D 43/00* (2006.01)
*H04L 12/40* (2006.01)
*C02F 1/32* (2006.01)

(52) U.S. Cl.
CPC ........ *H04L 12/40032* (2013.01); *B01D 43/00* (2013.01); *C02F 1/32* (2013.01); *H04L 2012/4026* (2013.01)

(58) Field of Classification Search
CPC .......... B01D 21/283; B01D 2021/0081; B01D 43/00; B01J 9/10; C02F 1/36; C21B 3/04
See application file for complete search history.

(56) References Cited

U.S. PATENT DOCUMENTS

2013/0302213 A1* 11/2013 Lipkens ................. B01D 43/00 422/119

* cited by examiner

*Primary Examiner* — Walter D Griffin
*Assistant Examiner* — Cameron Allen
(74) *Attorney, Agent, or Firm* — Richard M. Klein; Fay Sharpe LLP

(57) ABSTRACT

A method for separating a second fluid or a particulate from a host fluid is disclosed. The method includes flowing the mixture through an acoustophoretic device comprising an acoustic chamber, an ultrasonic transducer, and a reflector. The transducer includes a piezoelectric material driven by a voltage signal to create a multi-dimensional acoustic standing wave in the acoustic chamber. A voltage signal is sent to drive the ultrasonic transducer in a displacement profile that is a superposition of a combination of different mode shapes that are the same order of magnitude to create the multi-dimensional acoustic standing wave in the acoustic chamber such that the second fluid or particulate is continuously trapped in the standing wave, and then agglomerates, aggregates, clumps, or coalesces together, and subsequently rises or settles out of the host fluid due to buoyancy or gravity forces, and exits the acoustic chamber.

21 Claims, 15 Drawing Sheets

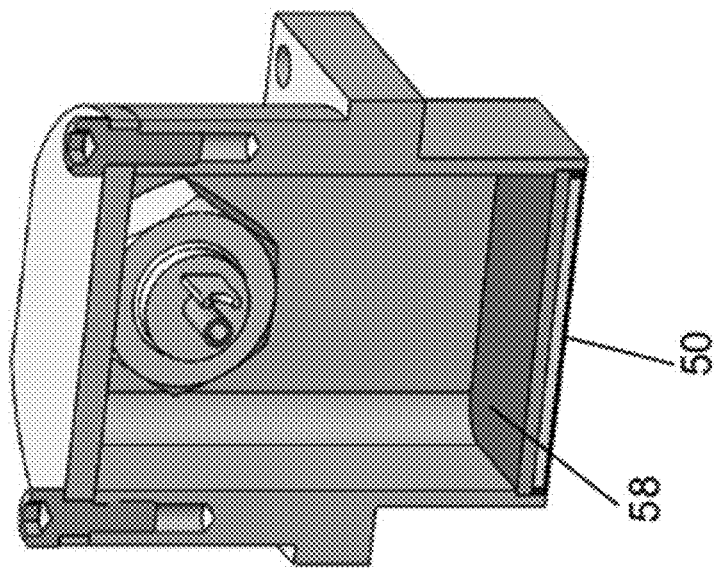
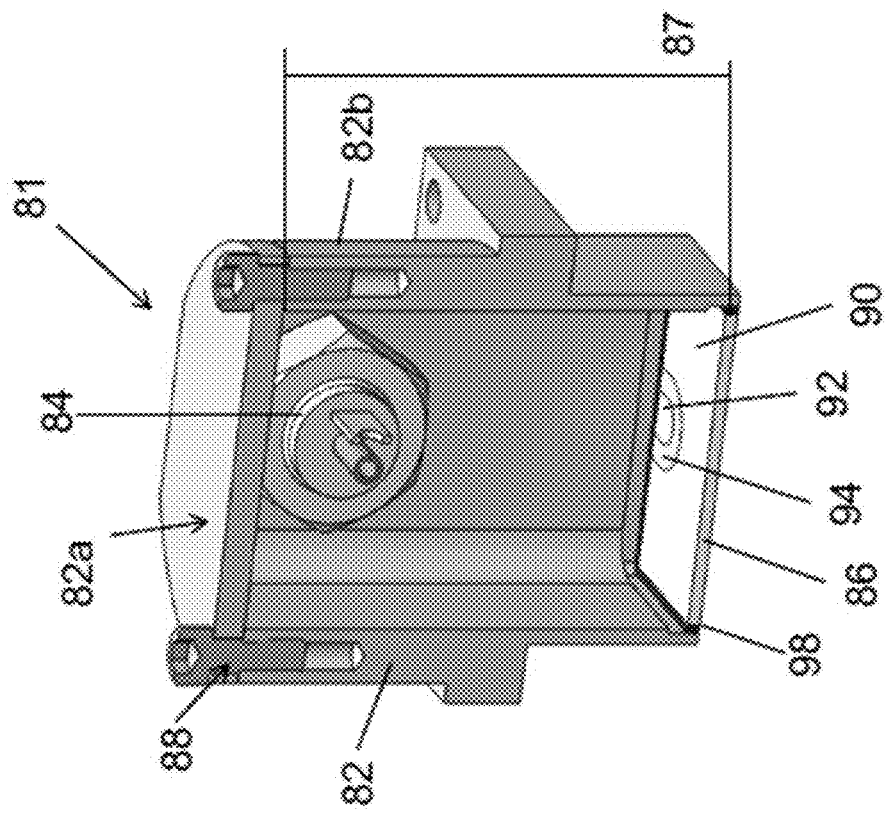

ACOUSTIC MANIPULATION OF PARTICLES IN STANDING WAVE FIELDS

CROSS-REFERENCE TO RELATED APPLICATIONS

This application is a continuation-in-part of U.S. patent application Ser. No. 15/161,108, filed on May 20, 2016, which claims priority to U.S. Provisional Patent Application Ser. No. 62/163,994, filed on May 20, 2015, the disclosures of which are hereby fully incorporated by reference in their entireties.

BACKGROUND

The subject matter described herein relates to the use of ultrasonically generated acoustic standing waves to achieve trapping, concentration, and separation of suspended-phase components and thereby remove such contaminants from a fluid medium such as water.

When particles are entrained or dispersed in a flowing fluid, aggregation of the particles to form larger clumps is typically due to some attraction or adhesion between the particles or the addition of a flocculating agent that aids in attracting and aggregating the particles. Attractive forces between the particles may be ionic or physical entanglement.

Typically, after the clumps of particles are formed in the fluid medium, a physical filtration process is utilized to separate the aggregated, agglomerated, flocculated or otherwise process-formed particle clumps. Most of the work reported in the literature for particle removal from water involves replaceable filter units consisting generally of packed cartridges, filter membranes, or special filter papers. If the separation process is a filter separation process, the physical filter media and the clumps of particles that have been separated from the fluid media are typically discarded, thus creating additional waste and increasing costs. Also, with the use of this physical filtration process, the yield of the filtrate is lessened, as some of it is used to saturate the filtering material. Further, as the filter fills up, filtration capacity is reduced, and using such filters may impose periodic stopping to remove the filter and obtain the particles trapped thereon. Finally, though particles over 10 micrometers can typically be captured by these techniques, smaller particles, such as bacterial spores in the size range of 1 micrometer, are typically not captured with sufficient efficiency.

Thus, methods are sought where continuous filtration may be carried out. Such continuous methods would be useful in various filtration applications, such as the filtering of oil from water, components from blood, tailings from water in tailing ponds, and, generally, particles from a fluid stream and immiscible or emulsified fluids from a fluid stream.

Acoustophoresis is the separation of particles and secondary fluids from a primary or host fluid using high intensity acoustic standing waves, and without the use of membranes or physical size exclusion filters. It has been known that high intensity standing waves of sound can exert forces on particles in a fluid when there is a differential in both density and/or compressibility, otherwise known as the acoustic contrast factor. The pressure profile in a standing wave contains areas of local minimum pressure amplitudes at its nodes and local maxima at its anti-nodes. Depending on the density and compressibility of the particles, they will be trapped at the nodes or anti-nodes of the standing wave. Generally, the higher the frequency of the standing wave, the smaller the particles that can be trapped due the pressure of the standing wave.

In conventional acoustophoretic devices, planar acoustic standing waves, with resonance frequencies of $n*c/2\ L$, where n is an integer, c is the speed of sound of the fluid, and L is the length of the acoustic resonator resonator or the length of the standing wave, have been used to accomplish the separation process. However, a single planar wave tends to trap the particles or secondary fluid in a manner such that they can only be separated from the primary fluid by turning off the planar standing wave. This does not allow for continuous operation. Also, the amount of power that is needed to generate the acoustic planar standing wave tends to heat the primary fluid through waste energy.

Conventional acoustophoresis devices have thus had limited efficacy due to several factors including heat generation, use of planar standing waves, limits on fluid flow, and the inability to capture different types of materials. It would therefore be desirable to provide systems and methods of generating optimized particle clusters to improve gravity separation and collection efficiency. Improved acoustophoresis devices using improved fluid dynamics would also be desirable, so the acoustophoresis can be a continuous process.

BRIEF DESCRIPTION

The present disclosure relates, in various embodiments, to acoustophoretic devices and methods of separating a second fluid or a particulate from a host fluid. Briefly, a superposition of multi-dimensional acoustic standing waves is used to continuously trap the second fluid or particulate, which then agglomerates, aggregates, clumps, or coalesces together, and subsequently rises or settles out of the host fluid due to buoyancy or gravity forces, and exits the acoustic chamber.

Method disclosed herein for separating a second fluid or a particulate from a host fluid comprise flowing a mixture of the host fluid and the second fluid or particulate through an acoustophoretic device. The acoustophoretic device comprises an acoustic chamber having at least one inlet and at least one outlet; at least one ultrasonic transducer located on a wall of the acoustic chamber, the at least one ultrasonic transducer including a piezoelectric material driven by a voltage signal to create a superposition of multi-dimensional acoustic standing waves in the acoustic chamber; and a reflector located on a wall on the opposite side of the acoustic chamber from the at least one ultrasonic transducer. The method further comprises sending a voltage signal to drive the at least one ultrasonic transducer in a displacement profile that is a superposition of a combination of different modes (such as planar, fundamental, and/or higher order mode shapes) that are the same order of magnitude to create the multi-dimensional acoustic standing wave in the acoustic chamber such that the second fluid or particulate is continuously trapped in the standing wave, and then agglomerates, aggregates, clumps, or coalesces together, and subsequently rises or settles out of the host fluid due to buoyancy or gravity forces, and exits the acoustic chamber.

Mode (1, 1) is known as the fundamental mode. The fundamental and higher order mode shapes may have peaks within 0.005 megahertz (MHz) of each other. The higher order mode shapes may include modes (1, 3); (1, 5); (3, 3); (3, 5); and (5, 5). In certain embodiments, the higher order modes may include modes up to (25, 25) and higher. The different modes may have peaks within a frequency interval between resonance frequencies of planar standing waves.

A frequency of excitation of the piezoelectric material can be changed or dithered over a small interval, exciting the piezoelectric material in multiple higher order modes, and then cycling the frequency back through lower modes of the piezoelectric material, thereby allowing for various multi-dimensional wave shapes, along with a single piston mode shape, to be generated over a designated time. In other embodiments, a frequency of excitation of the piezoelectric material is a fixed frequency excitation where a weighted combination of several modes contribute to the overall displacement profile of the piezoelectric element. The piezoelectric material may be configured to vibrate to create an acoustic pressure profile in the acoustic chamber in a direction that is orthogonal to a direction of propagation of the acoustic standing wave, the pressure profile including multiple maxima and minima.

In particular embodiments, the multi-dimensional standing wave results in an acoustic radiation force having an axial force component and a lateral force component that are the same order of magnitude. The multi-dimensional acoustic standing wave can be generated in the acoustic chamber normal to a direction of flow therethrough. The piezoelectric material can vibrate to create a pressure profile across the surface of the flowing mixture, the pressure profile having multiple maxima and minima. Hot spots in the mixture can be generated that are located at a minimum of the acoustic radiation potential. The voltage signal can have a sinusoidal, square, sawtooth, triangle, or pulsed waveform. The voltage signal can have a frequency of 100 kHz to 10 MHz. The voltage signal can be driven with amplitude or frequency modulation start/stop capability to eliminate acoustic streaming. The reflector may have a non-planar surface.

In some implementations, a multi-dimensional acoustic standing wave is generated between two or more acoustic transducers arranged to direct a generated acoustic wave toward each other. For example, the reflector may be replaced by an acoustic transducer that is capable of generating a multi-dimensional standing wave. The combination of transducers contributes to generating and reflecting acoustic waves to create a multi-dimensional standing wave. For example, the acoustic waves generated by the transducers can arranged to constructively and/or destructively interfere with each other to form a multi-dimensional standing wave.

In some implementations, an acoustic transducer pair, or acoustic transducer/reflector pair are configured to operate in multi-mode. Multi-mode operation provides for a number of modes being present at a certain operating point, such as a frequency operating point, for example. Multi-mode operation may occur at operating points between instances of single-mode operation. During multi-mode operation, a primarily dominant mode may be present, in addition to one or more secondary modes. The superposition of modes may contribute to forming a multi-dimensional acoustic standing wave, with lateral as well as axial acoustic radiation forces. The primary and secondary modes may vary depending on selected operating points, for example. When an acoustic transducer generates an acoustic wave that is reflected back to the transducer to create a standing wave, the reflected wave can act as a load on the acoustic transducer. The loading of the transducer, from a reflected wave or other sources of loading, such as a second acoustic transducer acoustically coupled through a fluid, can influence multi-mode operation. For example, a transducer load may change the frequency at which a given mode becomes dominant or peaks. A desired operating point for multi-mode operation, and the characteristics of the different modes, may thus be impacted by loading.

In certain constructions, the at least one ultrasonic transducer may comprise: a housing having a top end, a bottom end, and an interior volume; and a piezoelectric element at the bottom end of the housing having an exposed exterior surface and an interior surface, the piezoelectric element being able to vibrate when driven by a voltage signal. A backing layer can contact the interior surface of the piezoelectric element, the backing layer being made of a substantially acoustically transparent material. The substantially acoustically transparent material may be balsa wood, cork, or foam. The substantially acoustically transparent material may have a thickness of up to 1 inch. The substantially acoustically transparent material may be in the form of a lattice. An exterior surface of the piezoelectric element can be covered by a wear surface material with a thickness of a half wavelength or less, the wear surface material being a urethane, epoxy, or silicone coating. In some embodiments, the piezoelectric element has no backing layer or wear layer. The piezoelectric element can be a crystalline, semi-crystalline, or non-crystalline.

In the methods according to the present disclosure, the mixture of the second fluid or particulate can flow vertically downwards, and the second fluid or particulate can float upward to a collection duct. In alternative embodiments, the mixture can flow vertically upwards, and the second fluid or particulate can sink down to a collection duct. The particulate may be Chinese hamster ovary (CHO) cells, NS0 hybridoma cells, baby hamster kidney (BHK) cells, or human cells.

In particular embodiments, the acoustic standing wave may be a multi-dimensional acoustic standing wave. Examples of such multi-dimensional acoustic standing waves can be found in commonly owned U.S. Pat. No. 9,228,183, the entire contents of which are hereby fully incorporated by reference. In other embodiments, the acoustic standing wave can be a planar acoustic standing wave. Further yet, in particular embodiments, the acoustic standing wave may be a combination of a planar acoustic standing wave and a multidimensional acoustic standing wave, where the planar acoustic standing wave and multidimensional acoustic standing wave are super-positioned on each other.

Also disclosed herein are devices for separating a second fluid or a particulate from a host fluid, comprising: an acoustic chamber including at least one inlet and at least one outlet; at least one ultrasonic transducer coupled to the acoustic chamber to permit generation of an acoustic wave therein, the at least one ultrasonic transducer including a piezoelectric material configured to be driven so that the piezoelectric material vibrates in higher order modes of the general formula (m, n), wherein m and n are independently 1 or greater (or 3 or greater), to create a multi-dimensional acoustic standing wave in the acoustic chamber; and a reflector located opposite to the at least one ultrasonic transducer. The higher order modes may be of the same order of magnitude. The higher order modes can include at least two modes selected from the group consisting of modes (3, 3); (3, 5); and (5, 5).

Also described herein are devices for separating a second fluid or a particulate from a host fluid, comprising: an acoustic chamber including at least one inlet and at least one outlet; at least one ultrasonic transducer coupled to the acoustic chamber to permit generation of an acoustic wave therein, the at least one ultrasonic transducer including a piezoelectric material configured to be driven in a displacement profile that is a superposition of a combination of different modes to create a multi-dimensional acoustic standing wave in the acoustic chamber; where the multidimensional acoustic standing wave is the result of the perturbation of a PZT material having characteristics of a 33 orientation where the piezoelectric elements are characterized by independent λ values, independent e values, and independent ϵ values such that, in a resonant cavity with an acoustic standing wave, the electrical boundary conditions are defined by the following equations:

$$\varphi(x, y, z = d_z) = \sum_{n,m} V_{n,m} \cos k_{xn} x \cos k_{ym} y$$

$$\phi(x,y,z=0)=0$$

where V is the voltage amplitude, n is the periodic index, and m is the periodic index for the (n,m) mode of interest; and a reflector located across the acoustic chamber from the at least one ultrasonic transducer.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 8 is a cross-sectional diagram of an ultrasonic transducer according to the present disclosure. An air gap is present within the transducer, and no backing layer or wear plate is present.

FIG. 9 is a cross-sectional diagram of an ultrasonic transducer according to the present disclosure. An air gap is present within the transducer, and a backing layer and wear plate are present.

DETAILED DESCRIPTION

Figure 1:
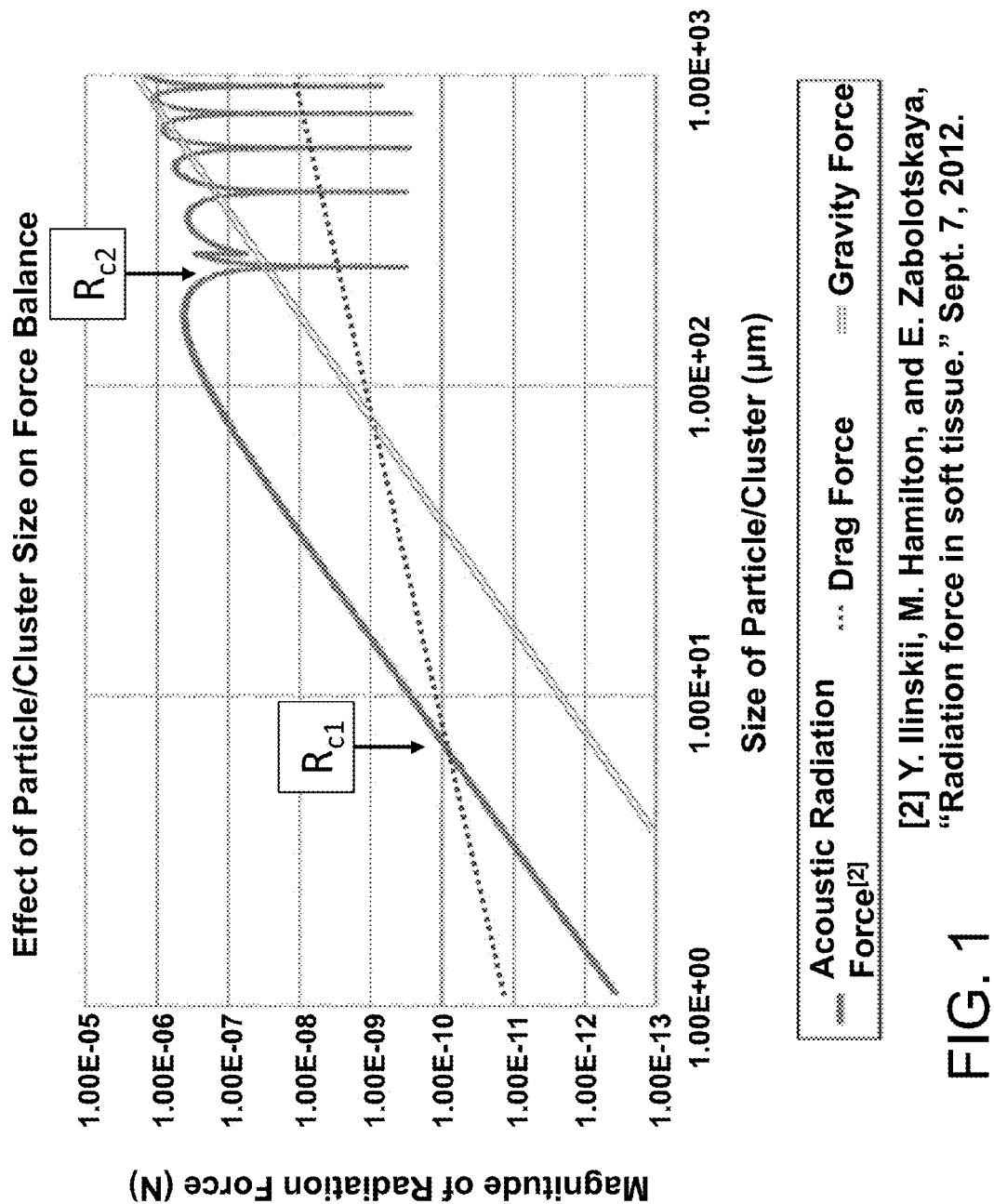
FIG. 1 is a graph showing the relationship of the acoustic radiation force, gravity/buoyancy force, and Stokes' drag force to particle size. The horizontal axis is in microns (μm) and the vertical axis is in Newtons (N).

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named component and allowing the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; upwards is always against the gravity of the earth.

The term "parallel" should be construed in its lay sense of two surfaces that maintain a generally constant distance between them, and not in the strict mathematical sense that such surfaces will never intersect when extended to infinity.

The present application refers to "the same order of magnitude." Two numbers are of the same order of magnitude if the quotient of the larger number divided by the smaller number is a value of at least 1 and less than 10.

Acoustophoresis is the separation of particles and secondary fluids from a primary or host fluid using high-intensity acoustic standing waves, and without the use of membranes or physical size exclusion filters. It has been known that high intensity standing waves of sound can exert forces on particles in a fluid when there is a differential in both density and/or compressibility, otherwise known as the acoustic contrast factor. The pressure profile in a standing wave contains areas of local minimum pressure amplitudes at its nodes and local maxima at its anti-nodes. Depending on the density and compressibility of the particles, they will be trapped at the nodes or anti-nodes of the standing wave. Generally, the higher the frequency of the standing wave, the smaller the particles that can be trapped due the pressure of the standing wave.

When acoustic standing waves propagate in liquids, the fast oscillations may generate a non-oscillating force on particles suspended in the liquid or on an interface between liquids. This force is known as the acoustic radiation force. The force originates from the non-linearity of the propagating wave. As a result of the non-linearity, the wave is distorted as it propagates and the time-averages are nonzero. By serial expansion (according to perturbation theory), the first non-zero term will be the second-order term, which accounts for the acoustic radiation force. The acoustic radiation force on a particle, or a cell, in a fluid suspension is a function of the difference in radiation pressure on either side of the particle or cell. The physical description of the radiation force is a superposition of the incident wave and a scattered wave, in addition to the effect of the non-rigid particle oscillating with a different speed compared to the surrounding medium thereby radiating a wave. The following equation presents an analytical expression for the acoustic radiation force on a particle, or cell, in a fluid suspension in a planar standing wave.

$$F_R = \frac{3\pi P_0^2 V_p \beta_m}{2\lambda} \varphi(\beta, \rho) \sin(2kx) \qquad (1)$$

where $\beta_m$ is the compressibility of the fluid medium, $\rho$ is density, $\phi$ is acoustic contrast factor, $V_p$ is particle volume, $\lambda$ is wavelength, k is $2\pi/\lambda$, $P_0$ is acoustic pressure amplitude, x is the axial distance along the standing wave (i.e., perpendicular to the wave front), and $$\varphi(\beta, \rho) = \frac{5\rho_\rho - 2\rho_m}{2\rho_\rho + \rho_m} - \frac{\beta_\rho}{\beta_m}$$

where $\rho_p$ is the particle density, $\rho_m$ is the fluid medium density, $\beta_p$ is the compressibility of the particle, and $\beta_m$ is the compressibility of the fluid medium.

For a multi-dimensional standing wave, the acoustic radiation force is a three-dimensional force field, and one method to calculate the force is Gor'kov's method, where the primary acoustic radiation force $F_R$ is defined as a function of a field potential U, $F_V = -\nabla(U)$, where the field potential U is defined as $$U = \frac{4}{3}\pi R_p^3 \left[ \frac{\langle p^2(x, y, z) \rangle}{2\rho_f c_f^2} f_1 - \frac{3\rho_f \langle v^2(x, y, z) \rangle}{4} f_2 \right]$$

and $f_1$ and $f_2$ are the monopole and dipole contributions defined by $$f_1 = 1 - \frac{1}{\Lambda \sigma^2} \quad f_2 = \frac{2(\Lambda - 1)}{2\Lambda + 1}$$

where $$\sigma = \frac{c_p}{c_f} \quad \Lambda = \frac{\rho_p}{\rho_f} \quad \beta_f = \frac{1}{\rho_f c_f^2}$$

where p is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o$ is the volume of the cell, and <> indicates time averaging over the period of the wave.

Gork'ov's model is for a single particle in a standing wave and is limited to particle sizes that are small with respect to the wavelength of the sound fields in the fluid and the particle. It also does not take into account the effect of viscosity of the fluid and the particle on the radiation force. As a result, this model cannot be used for macro-scale ultrasonic separators since particle clusters can grow quite large.

FIG. 1 is a log-log graph (logarithmic y-axis, logarithmic x-axis) that shows the scaling of the acoustic radiation force, fluid drag force, and buoyancy force with particle radius. Calculations are done for a typical mammalian cell used in experiments. In the experiment, the mammalian cell had a density ($\rho_p$) of 1,050 kg/m$^3$ and a cell sound speed ($c_p$) of 1,550 m/s. The fluid in which the particle was flowed was water having a density ($\rho_w$) of 1000 kg/m$^3$, a fluid sound speed ($c_f$) of 1500 m/s, and a flow rate ($v_f$) of 4 cm/min. The experiment used 33 PZT-8 ultrasonic transducers driven at a frequency (f) of 2.2 MHz at a pressure (p) of 1 MPa. As explained above, the gravity/buoyancy force is a particle volume dependent force, and is therefore negligible for particle sizes on the order of micron, but grows, and becomes significant for particle sizes on the order of hundreds of microns. The fluid drag force scales linearly with fluid velocity, and therefore typically exceeds the buoyancy force for micron sized particles, but is negligible for larger sized particles on the order of hundreds of microns. The acoustic radiation force scaling is different. When the particle size is small, Gor'kov's equation is accurate and the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when a suspension is flowing through the system with primarily small micron sized particles, it is necessary for the acoustic radiation force to balance the combined effect of fluid drag force and buoyancy force for a particle to be trapped in the standing wave. In FIG. 1, this happens for a particle size of about 3.5 micron, labeled as $R_{c1}$. The graph then indicates that all larger particles will be trapped as well. Therefore, when small particles are trapped in the standing wave, particles coalescence/clumping/aggregation/agglomeration takes place, resulting in continuous growth of effective particle size. As the particle size grows, the acoustic radiation force reflects off the particle, such that large particles will cause the acoustic radiation force to decrease. Particle size growth continues until the buoyancy force becomes dominant, which is indicated by a second critical particle size, $R_{c2}$, at which size the particles will rise or sink, depending on their relative density with respect to the host fluid. Thus, FIG. 1 explains how small particles can be trapped continuously in a standing wave, grow into larger particles or clumps, and then eventually will rise or settle out because of increased buoyancy force.

Figure 2:
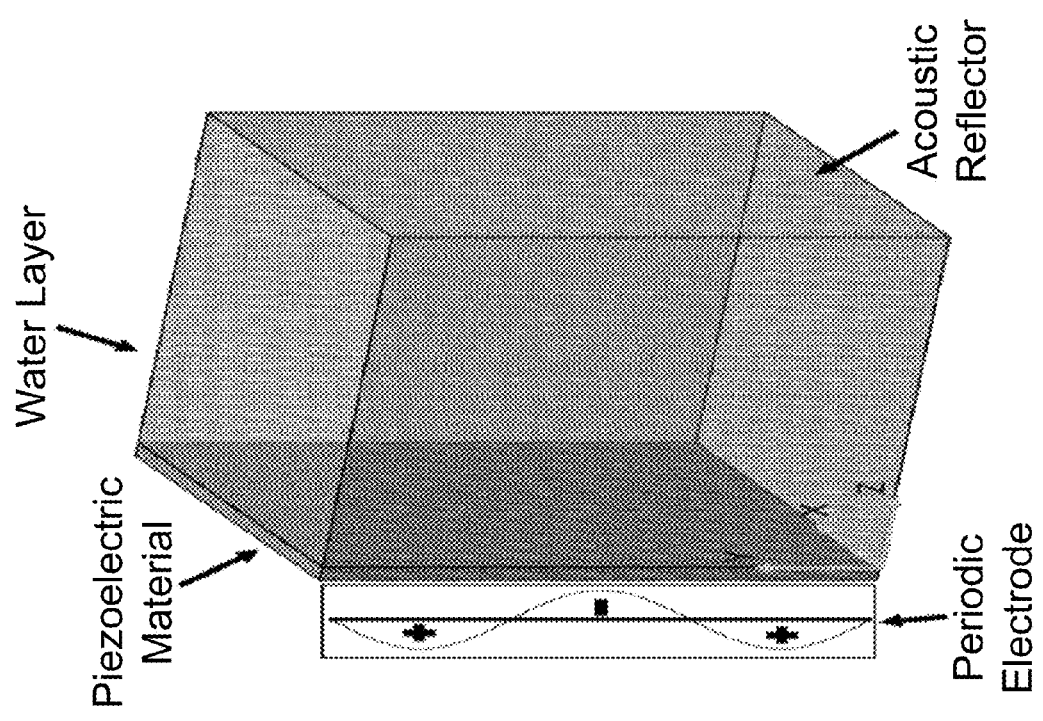
FIG. 2 illustrates a general configuration of a piezoelectric element separated from a reflective boundary layer by a water layer.

A more complex and complete model than for acoustic radiation forces that is not limited by particle size, like Gork'ov's model, may be used. The models that were implemented in the present disclosure are based on the theoretical work of Yurii Ilinskii and Evgenia Zabolotskaya as described in AIP Conference Proceedings, Vol. 1474-1, pp. 255-258 (2012). These models also include the effect of fluid and particle viscosity, and therefore are a more accurate calculation of the acoustic radiation force. FIG. 2 shows a very general configuration of a piezoelectric material with electrodes on its faces. One electrode is configured as a periodic electric potential electrode, while the other electrode is configured as a ground electrode. The piezoelectric material is located opposite an acoustic reflector that provides a reflective boundary condition. The reflector and piezoelectric material are separated by a water layer. The general formulation of the piezoelectric equations is:

$$-\rho\omega^2 u_i = \lambda_{iklm}\frac{\partial^2 u_l}{\partial x_m \partial x_k} = e_{jik}\frac{\partial^2 \varphi}{\partial x_j \partial x_k}$$

$$0 = e_{ikl}\frac{\partial^2 u_k}{\partial x_l \partial x_i} - \varepsilon_{ik}\frac{\partial^2 \varphi}{\partial x_i \partial x_k}$$

where p is the density, $\omega$ is the angular frequency, u is the displacement tensor, $\phi$ is the electric field potential, $\lambda$ is the elasticity tensor, e is the coupling tensor, and $\varepsilon$ is the permittivity tensor. Based on this general formulation, the assumed solutions of the piezoelectric equations are:

$$u_x = \tilde{u}_x \sin(k_x x)\cos(k_y y)e^{iKz}$$

$$u_y = \tilde{u}_y \sin(k_y y)\cos(k_x x)e^{iKz}$$

$$u_z = \tilde{u}_z \cos(k_x x)\cos(k_y y)e^{iKz}$$

$$\phi = \tilde{\phi} \cos(k_x x)\cos(k_y y)e^{iKz}$$

where $\tilde{u}$ and $\tilde{\phi}$ are the complex amplitude and k and K are the wave numbers of the piezoelectric element. For 33 oriented PZT-8 piezoelectric elements, there are five independent $\lambda$ values, three independent e values, and two independent $\varepsilon$ values.

The mechanical boundary conditions are defined by the following equations:

$$\sigma_{zz}(d_z) = \lambda_{13}\left(\frac{\partial u_x}{\partial x} + \frac{\partial u_y}{\partial y}\right) + \lambda_{33}\frac{\partial u_z}{\partial z} + e_{33}\frac{\partial \varphi}{\partial z} = 0$$

$$\sigma_{xz}(d_z) = \frac{1}{2}\lambda_{55}\left(\frac{\partial u_x}{\partial z} + \frac{\partial u_z}{\partial x}\right) + e_{15}\frac{\partial \varphi}{\partial x} = 0$$

$$\sigma_{yz}(d_Z) = \frac{1}{2}\lambda_{55}\left(\frac{\partial u_y}{\partial z} + \frac{\partial u_z}{\partial y}\right) + e_{15}\frac{\partial \varphi}{\partial y} = 0$$

$$\sigma_{zz}(0) = \lambda_{13}\left(\frac{\partial u_x}{\partial x} + \frac{\partial u_y}{\partial y}\right) + \lambda_{33}\frac{\partial u_z}{\partial z} + e_{33}\frac{\partial \varphi}{\partial z} = -p_w$$

$$\sigma_{xz}(0) = \frac{1}{2}\lambda_{55}\left(\frac{\partial u_x}{\partial z} + \frac{\partial u_z}{\partial x}\right) + e_{15}\frac{\partial \varphi}{\partial x} = 0$$

$$\sigma_{yz}(0) = \frac{1}{2}\lambda_{55}\left(\frac{\partial u_y}{\partial z} + \frac{\partial u_z}{\partial y}\right) + e_{15}\frac{\partial \varphi}{\partial y} = 0$$

$$p_w(z=0) = \frac{ip_w\omega^2}{\sqrt{k_w^2 - k_x^2 - k_y^2}}\frac{1 + K_R e^{2ik_x L}}{1 - K_R e^{2ik_x L}}u_z(z=0)$$

where $\sigma$ is the stress, $d_z$ is the thickness of the piezoelectric element, $p_w$ is the acoustic pressure in water, $\rho_w$ is the density of water, $k_w$ is the wave number in water, $K_R$ is the reflection coefficient, and L is the length of the water layer.

The electrical boundary conditions are defined by the following equations:

$$\varphi(x, y, z=d_z) = \sum_{n,m} V_{n,m}\cos k_{xn}x \cos k_{ym}y$$

$$\phi(x,y,z=0)=0$$

where V is the voltage amplitude, n is the periodic index, and m is the periodic index for the (n,m) mode of interest.

The acoustophoretic separation technology of the present disclosure employs multi-dimensional ultrasonic acoustic standing waves, planar acoustic standing waves or combinations, i.e., superpositions, of planar and multidimensional acoustic standing waves (collectively referred to herein simple as acoustic standing waves) to trap particles or a secondary fluid in a volume of fluid containing said particles/secondary fluid.

Figure 3:
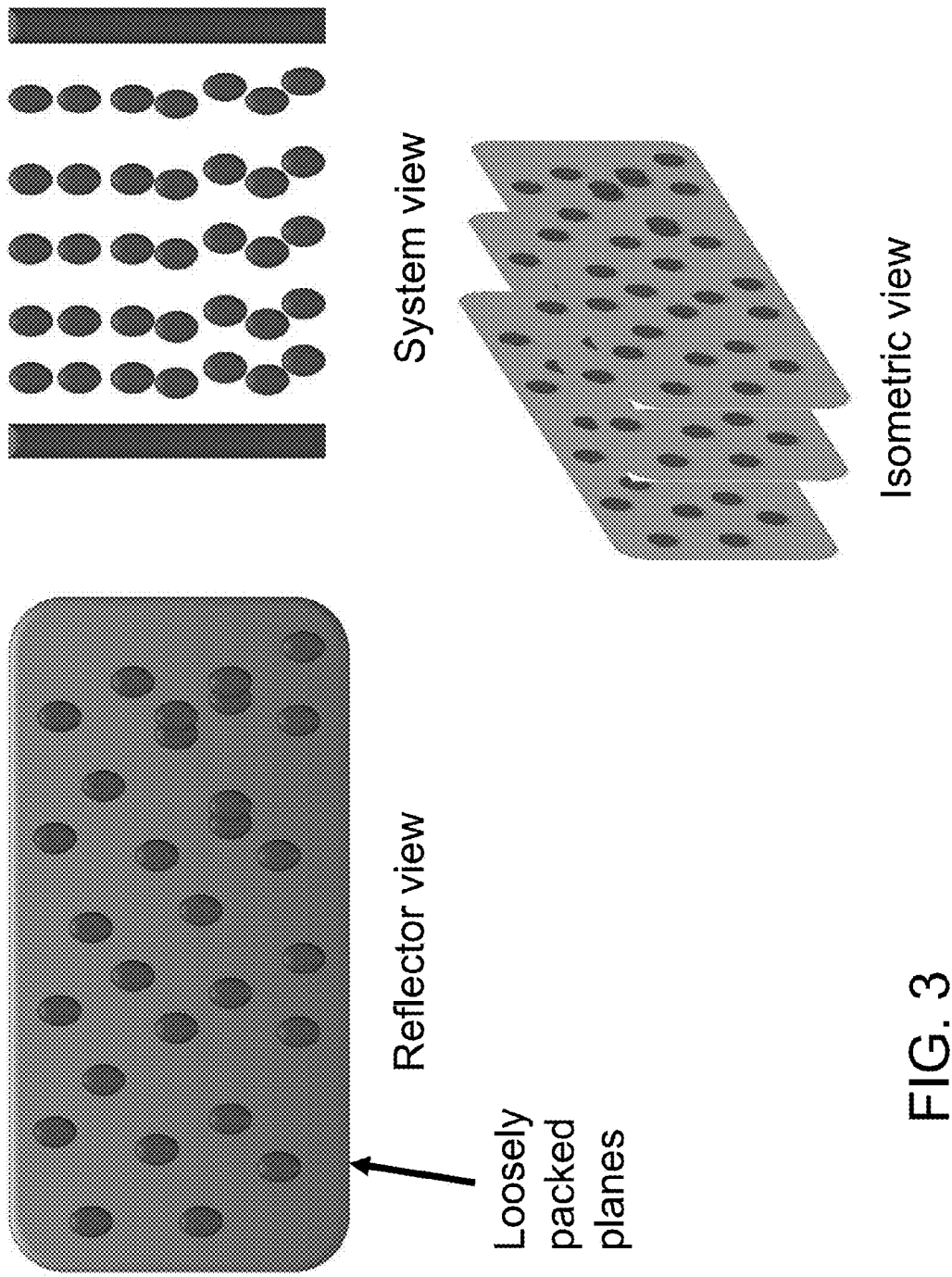
FIG. 3 presents the traditional approach of utilizing a transducer and reflector to generate a planar standing wave to create loosely packed planes of particles in an acoustic chamber. Three views are seen: a reflector view, a system view, and an isometric view.

FIG. 3 presents the traditional approach of utilizing a transducer and reflector located opposite one another to generate a planar standing wave therebetween. The left side of FIG. 3 presents a view of the acoustic chamber as seen through the reflector, while the middle picture of FIG. 3 presents a system view of the acoustic chamber from above. As can be seen in FIG. 3, the generation of a planar standing wave in an acoustic chamber results in the creation of loosely packed planes of particles in the acoustic chamber, typically corresponding to the pressure nodal planes for particles with positive acoustic contrast.

Figure 4:
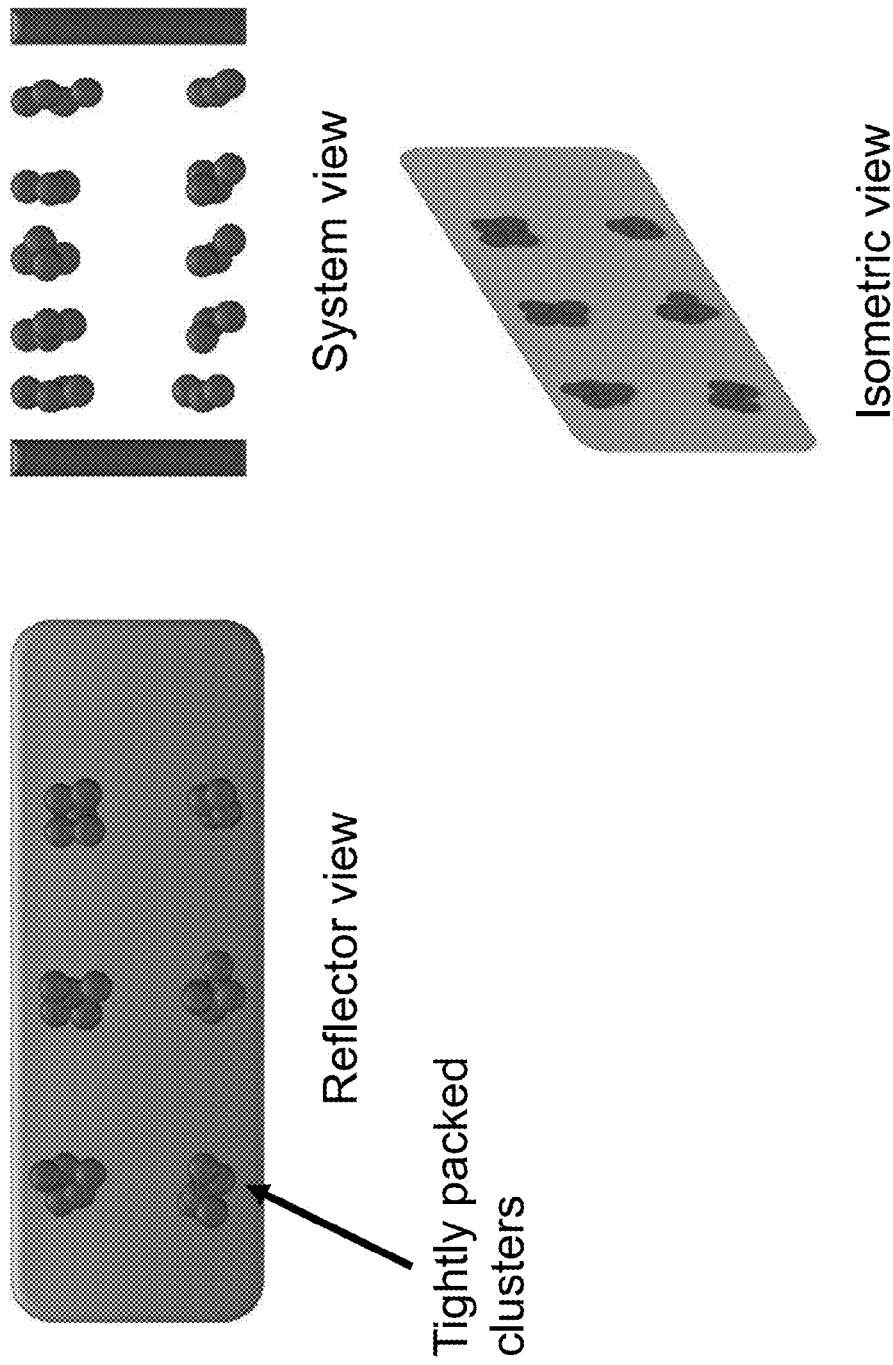
FIG. 4 presents a new approach according to the present disclosure of utilizing a transducer and reflector to generate a multi-dimensional acoustic standing wave to create tightly packed cluster of particles in an acoustic chamber. Three views are seen: a reflector view, a system view, and an isometric view.

FIG. 4, on the other hand, presents a new approach of utilizing a transducer and reflector located opposite one another to generate a multi-dimensional acoustic standing wave therebetween, or a superposition of multi-dimensional acoustic standing waves. As with FIG. 3, the left side of FIG. 4 presents a view of the acoustic chamber as seen through the reflector, while the middle picture of FIG. 4 presents a system view of the acoustic chamber from above. As can be seen in FIG. 4, the generation of a multi-dimensional acoustic standing wave in an acoustic chamber results in the creation of tightly packed clusters of particles in the acoustic chamber, typically corresponding to the location of the pressure nodes or anti-nodes in the standing wave depending on acoustic contrast factor.

The particles or secondary fluid collect at the nodes or anti-nodes of the acoustic standing wave, depending on the particles' or secondary fluid's acoustic contrast factor relative to the host fluid, forming clusters/clumps/agglomerates/coalesced droplets that continuously fall out of the acoustic standing wave when the clusters have grown to a size large enough to overcome the holding force of the acoustic standing wave (e.g. by coalescence or agglomeration) and the particle/secondary fluid density is higher than the host fluid, or to rise out of the acoustic standing wave when the particle/secondary fluid density is less than the host fluid. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable axial positions within the standing waves. When the acoustic radiation force exerted on the particles is stronger than the combined effect of fluid drag force and buoyancy and gravitational force, the particle is trapped within the acoustic standing wave field. This results in concentration, agglomeration and/or coalescence of the trapped particles. The strong lateral forces create rapid clustering of particles. Micron-sized particles, e.g., bacteria, mammalian cells, micro-algae, metal particles, yeast, fungi, lipids, oil droplets, red blood cells, white blood cells, platelets, etc., can thus be separated from the host fluid through enhanced gravitational separation. For the case of a suspension with several different particle sizes, it is possible by tuning of the system parameters to settle out the group of particles that are larger in size whereas the group of particles smaller in size can be kept in suspension. These two layers can then be harvested separately. A repeated process can then be used to fractionate groups of different sized particles according to size. In this regard, the multi-dimensional acoustic standing waves generated by each transducer can be of different frequencies.

One specific application for the acoustophoresis device is in the processing of bioreactor materials. It is important to be able to separate relatively larger cells and cell debris from the expressed materials that are in the host fluid. The expressed materials are composed of biomolecules such as recombinant proteins or monoclonal antibodies, and are the desired product to be recovered. Through the use of acoustophoresis, the separation of the cells and cell debris is very efficient and leads to very little loss of the expressed materials. This is an improvement over current filtration processes (depth filtration, tangential flow filtration, and the like), which show limited efficiencies at high cell densities, so that the loss of the expressed materials in the filter beds themselves can be up to 5% of the materials produced by the bioreactor. The use of mammalian cell cultures including Chinese hamster ovary (CHO), NS0 hybridoma cells, baby hamster kidney (BHK) cells, insect cells, and human cells (e.g. T-cells, B-cells, stem cells, red blood cells), and living/biological cells in general has proven to be a very efficacious way of producing/expressing the recombinant proteins and monoclonal antibodies used with today's pharmaceuticals. The filtration of the mammalian cells and the mammalian cell debris through acoustophoresis aids in greatly increasing the yield of the bioreactor. As desired, the acoustophoresis process may also be coupled with a standard filtration process upstream or downstream, such as depth filtration, tangential flow filtration (TFF), or other physical filtration processes.

In this regard, the acoustic contrast factor is a function of the ratio of particle to fluid compressibility and particle to fluid density. Most cell types present a higher density and lower compressibility than the medium in which they are suspended, so that the acoustic contrast factor between the cells and the medium has a positive value. As a result, the axial acoustic radiation force (ARF) drives the cells, with a positive contrast factor, to the pressure nodal planes, whereas cells or other particles with a negative contrast factor are driven to the pressure anti-nodal planes. The radial or lateral component of the ARF is larger than the combined effect of fluid drag force and gravitational force. The radial or lateral component drives the cells/particles to specific locations (points) within these planes where they cluster, clump, agglomerate, or coalesce into larger groups, which will then continuously gravity separate from the fluid.

Desirably, the ultrasonic transducer(s) generate a three-dimensional or multi-dimensional acoustic standing wave in the fluid that exerts a lateral force on the suspended particles to accompany the axial force so as to increase the particle trapping and clumping capabilities of the standing wave. Typical results published in literature state that the lateral force is two orders of magnitude smaller than the axial force. In contrast, the technology disclosed in this application provides for a lateral force to be of the same order of magnitude as the axial force (i.e. a multi-dimensional acoustic standing wave). However, in certain embodiments described further herein, combinations of transducers that produce both multi-dimensional acoustic standing waves and planar standing waves are contemplated. For purposes of this disclosure, a standing wave where the lateral force is of the same order of magnitude as the axial force is considered a "multi-dimensional acoustic standing wave."

It may be necessary, at times, due to acoustic streaming, to modulate the frequency or voltage amplitude of the standing wave. This may be done by amplitude modulation and/or by frequency modulation. The duty cycle of the propagation of the standing wave may also be utilized to achieve certain results for trapping of materials. In other words, the acoustic beam may be turned on and shut off at different frequencies to achieve desired results.

Figure 5:
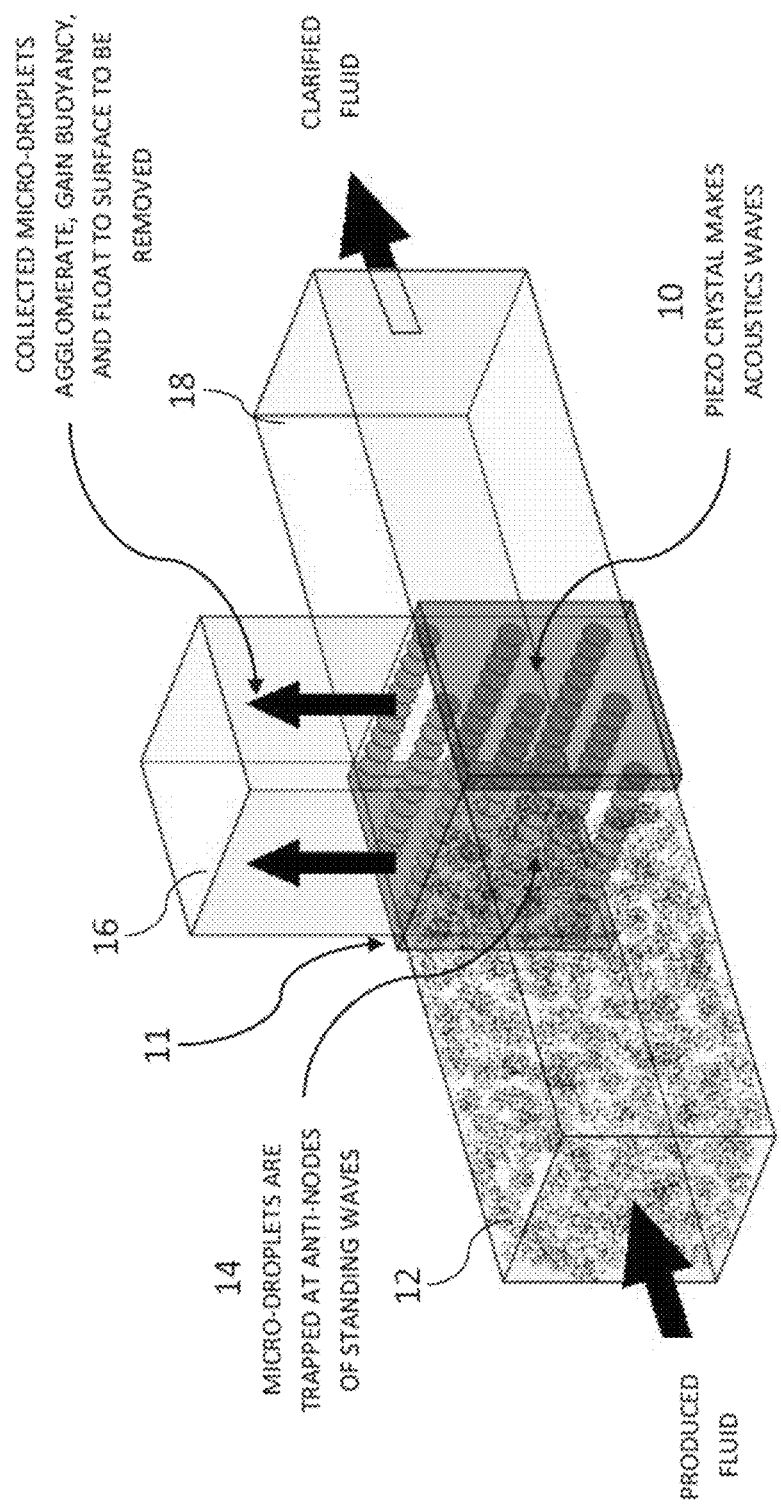
FIG. 5 is a diagram illustrating an acoustophoretic separation method according to the present disclosure for a second fluid or particle less dense than a host fluid.

A diagrammatic representation of an embodiment for removing oil or other lighter-than-water material is shown in FIG. 5. Excitation frequencies typically in the range from hundreds of kHz to 10s of MHz are applied by transducer 10. One or more standing waves are created between the transducer 10 and the reflector 11. In some configurations, reflector 11 can be implemented as an acoustic transducer, similar to or different from transducer 10, to form the acoustic standing waves there between. Microdroplets 12 are trapped in standing waves at the pressure anti-nodes 14 where they agglomerate, aggregate, clump, or coalesce, and, in the case of buoyant material, float to the surface and are discharged via an effluent outlet 16 located above the flow path. Clarified water is discharged at outlet 18. The acoustophoretic separation technology can accomplish multicomponent particle separation without any fouling at a much reduced cost.

Figure 6:
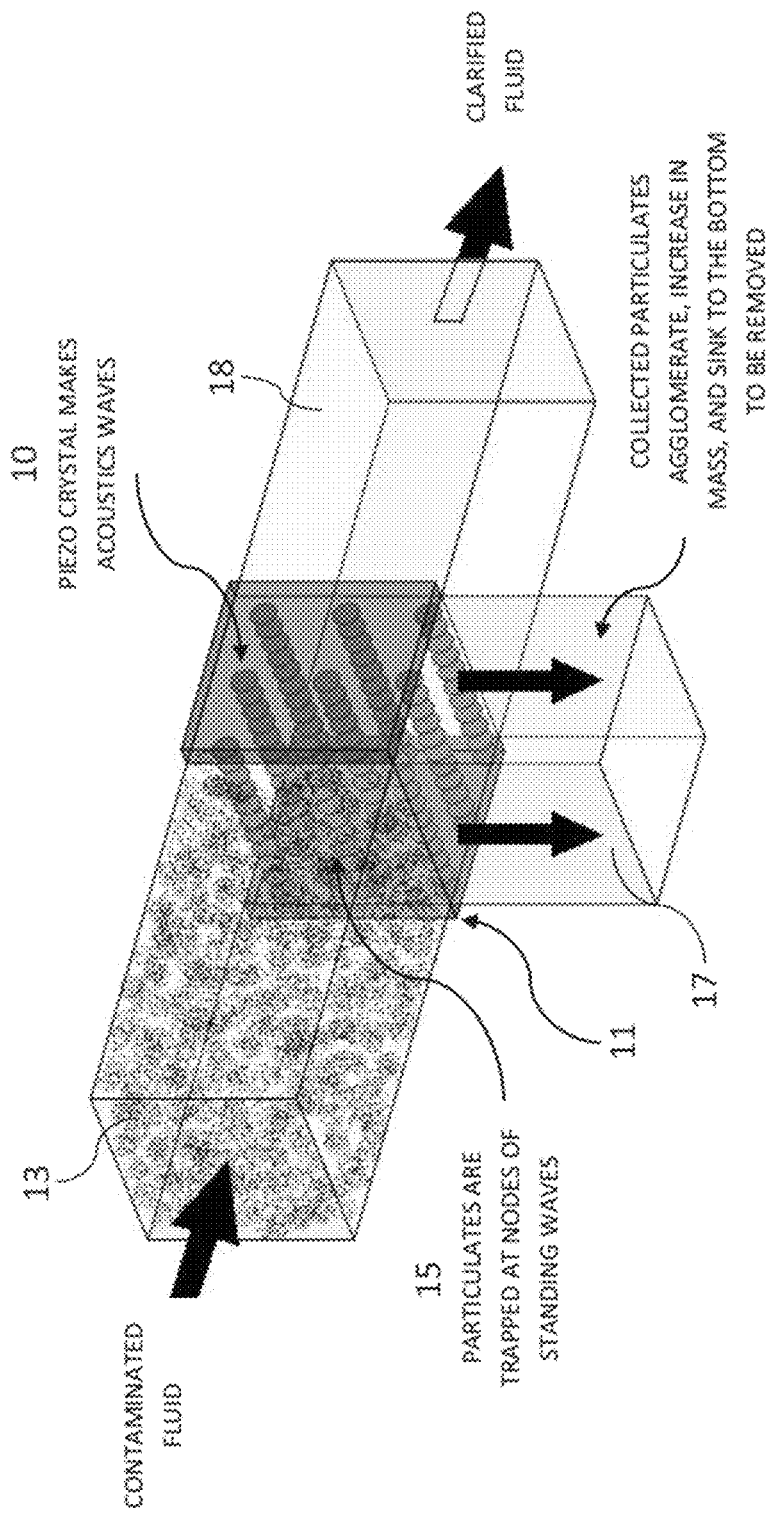
FIG. 6 is a diagram illustrating an acoustophoretic separation method according to the present disclosure for a second fluid or particle denser than a host fluid.

A diagrammatic representation of an embodiment for removing contaminants or other heavier-than-water material is shown in FIG. 6. Excitation frequencies typically in the range from hundreds of kHz to 10s of MHz are applied by transducer 10. An acoustic wave is generated by transducer 10 and propagates to reflector 11, which reflects the acoustic wave to create an acoustic standing wave. Reflector 11 can be implemented as an acoustic transducer, similar to or different from transducer 10, and can be actuated to contribute to generating an acoustic standing wave in conjunction with transducer 10. Contaminants in the incoming water 13 are trapped in standing waves at the pressure nodes 15 where they agglomerate, aggregate, clump, or coalesce, and, in the case of heavier material, sink to the bottom collector and are discharged via an effluent outlet 17 located below the flow path. Clarified water is discharged at outlet 18.

As previously explained, the ultrasonic transducer and reflector are located on opposite sides of the acoustic chamber. In this way, one or more acoustic standing waves are created between the ultrasonic transducer and reflector.

Prior to discussing further optimization of the systems, it is helpful to provide an explanation now of how multi-dimensional acoustic standing waves are generated. The multi-dimensional acoustic standing wave needed for particle collection is obtained by driving an ultrasonic transducer at a frequency that both generates the acoustic standing wave and excites a fundamental 3D vibration mode of the transducer piezoelectric element. Perturbation of the piezoelectric element in an ultrasonic transducer in a multimode fashion allows for generation of a multidimensional acoustic standing wave. A piezoelectric element can be specifically designed to deform in a multimode fashion at designed frequencies, allowing for generation of a multi-dimensional acoustic standing wave. The multi-dimensional acoustic standing wave may be generated by distinct modes of the piezoelectric element such as a 3×3 mode that would generate multidimensional acoustic standing waves. A multitude of multidimensional acoustic standing waves may also be generated by allowing the piezoelectric element to vibrate through many different mode shapes. Thus, the element would excite multiple modes such as a 0x0 mode (i.e. a piston mode) to a 1x1 (the fundamental mode), to 2x2, 1x3, 3x1, 3x3, and other higher order modes and then cycle back through the lower modes of the element (not necessarily in straight order). This switching or dithering of the piezoelectric element between modes allows for various multi-dimensional wave shapes, along with a single piston mode shape, to be generated over a designated time.

It is also possible to excite or choose a frequency of excitation that excites multiple modes at the same time, each mode with a varying degree of displacement amplitude. Through this combination of multiple modes excited at the same time with varying displacement amplitude, it is possible to generate a superposition of multi-dimensional standing waves desirable for trapping, clustering, and separation of a secondary fluid or particle from a host fluid.

The scattering of the acoustic field off the particles results in a three dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). When the acoustic radiation force exerted on the particles is stronger than the combined effect of fluid drag force and buoyancy and gravitational force, the particles are trapped within the acoustic standing wave field. This results in concentration, agglomeration and/or coalescence of the trapped particles. Relatively large solids of one material can thus be separated from smaller particles of a different material, the same material, and/or the host fluid through enhanced gravitational separation.

The multi-dimensional standing wave generates acoustic radiation forces in both the axial direction (i.e., in the direction of the standing wave, between the transducer and the reflector, perpendicular to the flow direction) and the lateral direction (i.e., in the flow direction). As the mixture flows through the acoustic chamber, particles in suspension experience a strong axial force component in the direction of the standing wave. Since this acoustic force is perpendicular to the flow direction and the drag force, it quickly moves the particles to pressure nodal planes or anti-nodal planes, depending on the contrast factor of the particle. The lateral acoustic radiation force then acts to move the concentrated particles towards the center of each planar node, resulting in agglomeration or clumping. The lateral acoustic radiation force component may overcome fluid drag for such clumps of particles to continually grow and then drop out of the mixture due to gravity. Therefore, both the drop in drag per particle as the particle cluster increases in size, as well as the drop in acoustic radiation force per particle as the particle cluster grows in size, may be considered for operation of the acoustic separator device. In the present disclosure, the lateral force component and the axial force component of the multi-dimensional acoustic standing wave are of the same order of magnitude. In this regard, it is noted that in a multi-dimensional acoustic standing wave, the axial force is stronger than the lateral force, but the lateral force of a multi-dimensional acoustic standing wave is much higher than the lateral force of a planar standing wave, usually by two orders of magnitude or more.

Some further explanation of the ultrasonic transducers used in the devices, systems, and methods of the present disclosure may be helpful as well. In this regard, the transducers use a piezoelectric element, usually made of PZT-8 (lead zirconate titanate). Such elements may have a 1 inch cross-section and a nominal 2 MHz resonance frequency, and may also be of a larger size. Each ultrasonic transducer module can have only one piezoelectric element, or can have multiple elements that each act as a separate ultrasonic transducer and are either controlled by one or multiple amplifiers. The piezoelectric element(s) can be crystalline, semi-crystalline, or non-crystalline. The piezoelectric element(s) can be square, rectangular, irregular polygon, or generally of any arbitrary shape. The transducer(s) is/are used to create a pressure field that generates forces of the same order of magnitude both orthogonal to the standing wave direction (lateral) and in the standing wave direction (axial).

Figure 7:
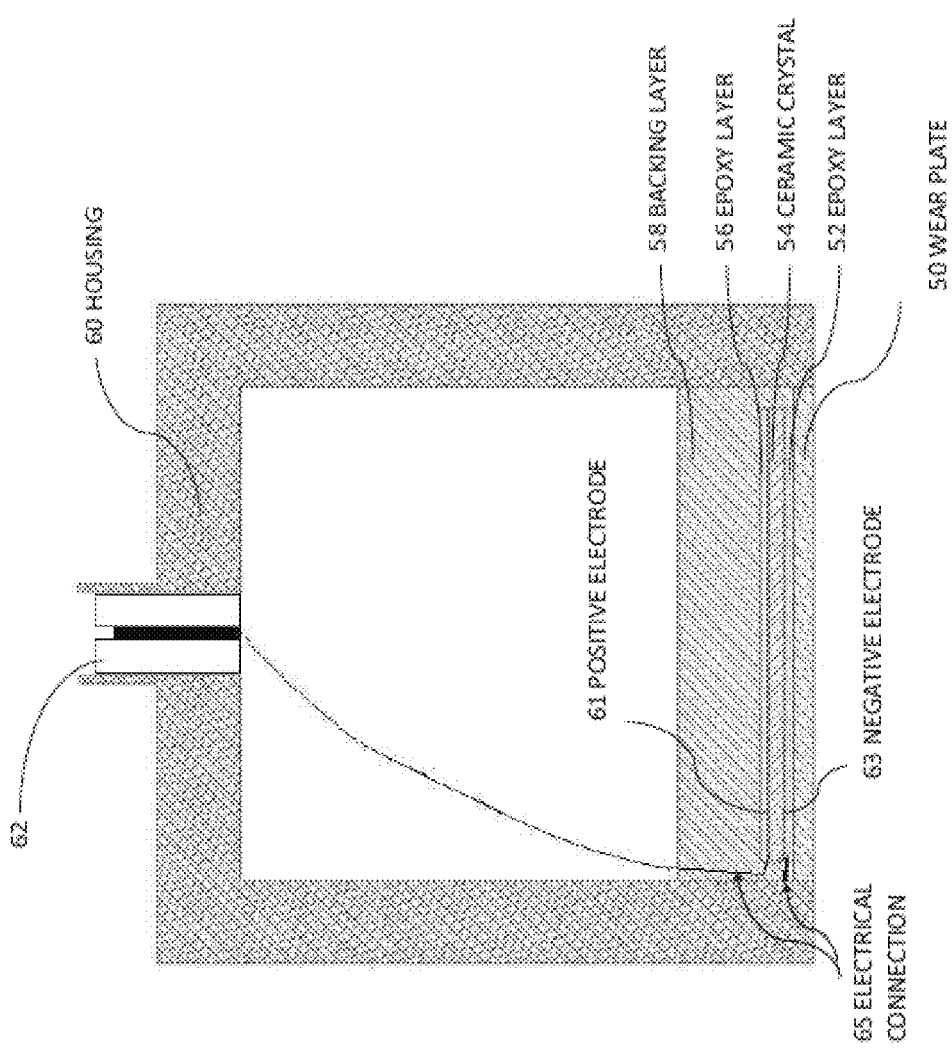
FIG. 7 is a cross-sectional diagram of a conventional ultrasonic transducer.

FIG. 7 is a cross-sectional diagram of a conventional ultrasonic transducer. This transducer has a wear plate 50 at a bottom end, epoxy layer 52, piezoelectric element 54 (e.g. a ceramic crystal made of, e.g. PZT), an epoxy layer 56, and a backing layer 58. On either side of the piezoelectric element, there is an electrode: a positive electrode 61 and a negative electrode 63. The epoxy layer 56 attaches backing layer 58 to the piezoelectric element 54. The entire assembly is contained in a housing 60 which may be made out of, for example, aluminum. An electrical adapter 62 provides connection for wires to pass through the housing and connect to leads (not shown) which attach to the piezoelectric element 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

FIG. 8 is a cross-sectional view of an ultrasonic transducer 81 of the present disclosure. Transducer 81 is shaped as a disc or a plate, and has an aluminum housing 82. The piezoelectric element can be, e.g., a mass of perovskite ceramic crystals, each consisting of a small, tetravalent metal ion, usually titanium or zirconium, in a lattice of larger, divalent metal ions, usually lead or barium, and O2- ions. As an example, in the embodiment shown in FIG. 8, a PZT (lead zirconate titanate) crystal 86 defines the bottom end of the transducer, and is exposed from the exterior of the housing. The crystal is supported on its perimeter by a small elastic layer 98, e.g. silicone or similar material, located between the crystal and the housing. Put another way, no wear layer is present. In particular embodiments, the crystal is an irregular polygon, and in further embodiments is an asymmetrical irregular polygon.

Screws 88 attach an aluminum top plate 82a of the housing to the body 82b of the housing via threads. The top plate includes a connector 84 for powering the transducer. The top surface of the PZT crystal 86 is connected to a positive electrode 90 and a negative electrode 92, which are separated by an insulating material 94. The electrodes can be made from any conductive material, such as silver or nickel. Electrical power is provided to the PZT crystal 86 through the electrodes on the crystal. Note that the crystal 86 has no backing layer or epoxy layer. Put another way, there is an air gap 87 in the transducer between aluminum top plate 82a and the crystal 86 (i.e. the air gap is completely empty). A minimal backing 58 and/or wear plate 50 may be provided in some embodiments, as seen in FIG. 9.

The transducer design can affect performance of the system. A typical transducer is a layered structure with the piezoelectric element bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the piezoelectric element to vibrate in one of its eigenmodes (i.e. near eigenfrequency) with a high Q-factor. The vibrating piezoelectric element, such as, e.g., a ceramic crystal/disk, is directly exposed to the fluid flowing through the acoustic chamber.

Removing the backing (e.g. making the piezoelectric element air backed) also permits the element to vibrate at higher order modes of vibration with little damping (e.g. higher order modal displacement). In a transducer having a piezoelectric element with a backing, the element vibrates with a more uniform displacement, like a piston. Removing the backing allows the element to vibrate in a non-uniform displacement mode. The higher order the mode shape of the piezoelectric element, the more nodal lines the element has. The higher order modal displacement of the element creates more trapping lines, although the correlation of trapping line to node is not necessarily one to one, and driving the element at a higher frequency will not necessarily produce more trapping lines.

In some embodiments, the piezoelectric element may have a backing that minimally affects the Q-factor of the crystal (e.g. less than 5%). The backing may be made of a substantially acoustically transparent material such as balsa wood, foam, or cork which allows the element to vibrate in a higher order mode shape and maintains a high Q-factor while still providing some mechanical support for the element. The backing layer may be a solid, or may be a lattice having holes through the layer, such that the lattice follows the nodes of the vibrating element in a particular higher order vibration mode, providing support at node locations while allowing the rest of the element to vibrate freely. The goal of the lattice work or acoustically transparent material is to provide support without lowering the Q-factor of the piezoelectric element or interfering with the excitation of a particular mode shape.

Placing the piezoelectric element in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymers or polymer films. Organic and biocompatible coatings such as silicone or polyurethane are also usable as a wear surface.

Perturbation of the piezoelectric element in an ultrasonic transducer in a multimode fashion allows for generation of a multi-dimensional acoustic standing wave. A piezoelectric element can be specifically designed to deform in a multi-mode fashion at designed frequencies, allowing for generation of a multi-dimensional acoustic standing wave. The multi-dimensional acoustic standing wave may be generated by distinct modes of the piezoelectric element such as the 3x3 mode that would generate multi-dimensional acoustic standing waves. A multitude of multi-dimensional acoustic standing waves may also be generated by allowing the piezoelectric element to vibrate through many different mode shapes by changing frequency over a small interval. Thus, the piezoelectric element would excite multiple modes such as a 0x0 mode (i.e. a piston mode) to a 1x1, 2x2, 1x3, 3x1, 3x3, and other higher order modes and then cycle back through the lower modes of the piezoelectric element (not necessarily in straight order). This switching or dithering of the piezoelectric element between modes allows for various multi-dimensional wave shapes, along with a single piston mode shape, to be generated over a designated time. In other embodiments, the excitation is a fixed frequency excitation where a weighted combination of several modes contribute to the overall displacement profile of the piezoelectric element. The lateral force of the total acoustic radiation force (ARF) generated by the ultrasonic transducers of the present disclosure is significant and is sufficient to overcome the fluid drag force at high linear velocities up to 1 cm/s and beyond. For example, linear velocities through the devices of the present disclosure can be a minimum of 4 cm/min for separation of cells/particles, and can be as high as 1 cm/sec for separation of oil/water phases.

The lateral force of the acoustic radiation force generated by the transducer can be increased by driving the transducer in higher order mode shapes, as opposed to a form of vibration where the piezoelectric element effectively moves as a piston having a uniform displacement. The acoustic pressure is proportional to the driving voltage of the transducer. The electrical power is proportional to the square of the voltage. The transducer is typically a thin piezoelectric plate, with electric field in the z-axis and primary displacement in the z-axis. The transducer is typically coupled on one side by air (i.e., the air gap within the transducer) and on the other side by the fluid mixture of the cell culture media. The types of waves generated in the plate are known as composite waves. A subset of composite waves in the piezoelectric plate is similar to leaky symmetric (also referred to as compressional or extensional) Lamb waves. The piezoelectric nature of the plate typically results in the excitation of symmetric Lamb waves. The waves are leaky because they radiate into the water layer, which result in the generation of the acoustic standing waves in the water layer. Lamb waves exist in thin plates of infinite extent with stress free conditions on its surfaces. Because the transducers of this embodiment are finite in nature, the actual modal displacements are more complicated.

Figure 10:
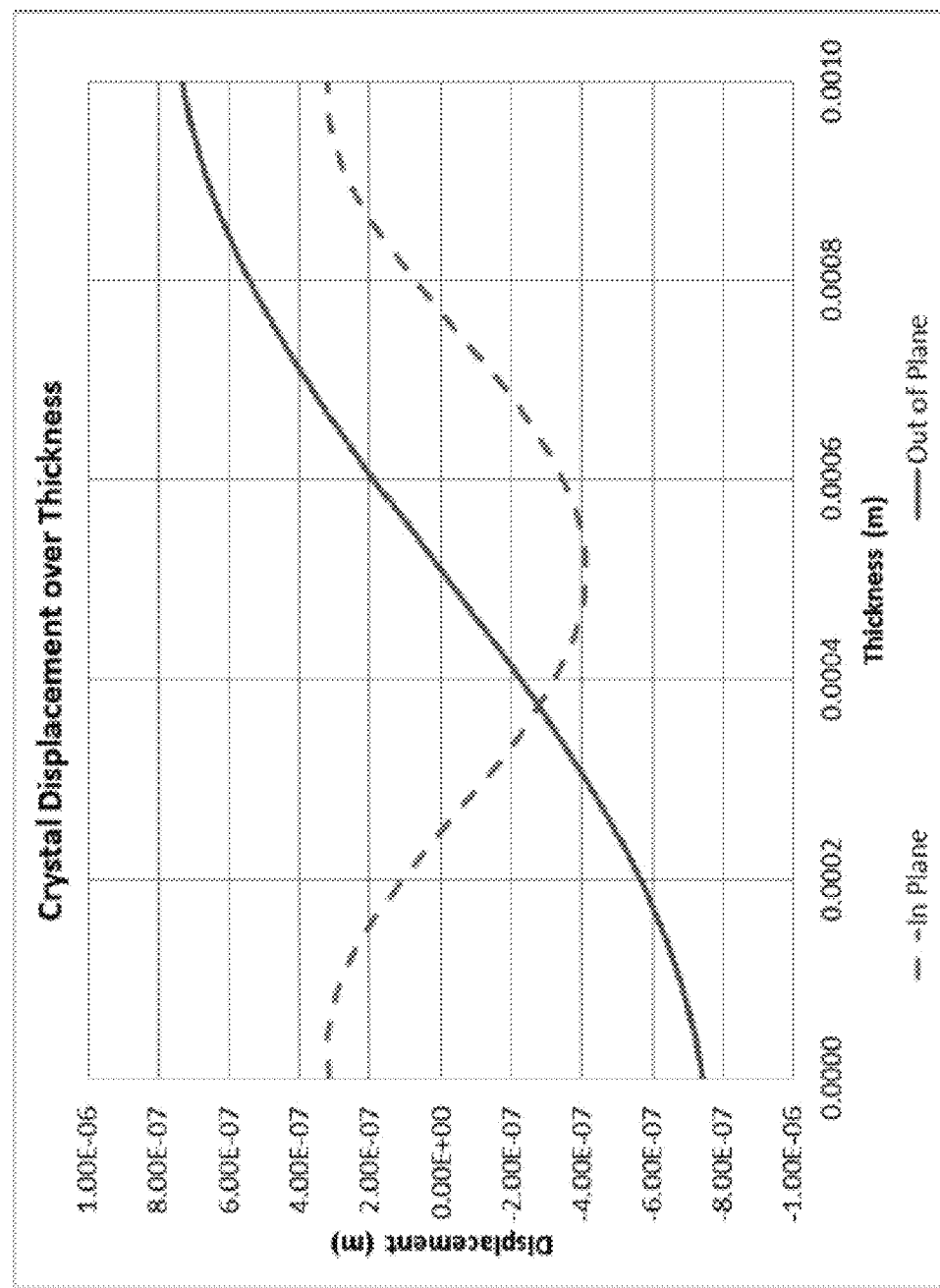
FIG. 10 shows the In-Plane and Out-of-Plane displacement of a piezoelectric crystal where composite waves are present.

FIG. 10 shows the typical variation of the in-plane displacement (x-displacement) and out-of-plane displacement (y-displacement) across the thickness of the plate, the in-plane displacement being an even function across the thickness of the plate and the out-of-plane displacement being an odd function. Because of the finite size of the plate, the displacement components vary across the width and length of the plate. In general, a (m,n) mode is a displacement mode of the transducer in which there are m undulations in transducer displacement in the width direction and n undulations in the length direction, and with the thickness variation, as described in FIG. 10. The maximum number of m and n is a function of the dimension of the piezoelectric element and the frequency of excitation. Additional three-dimensional modes exist that are not of the form (m,n).

The transducers are driven so that the piezoelectric element vibrates in higher order modes of the general formula (m, n), where m and n are independently 1 or greater. In particular embodiments, the piezoelectric element vibrates in at least three modes: modes (1, 1); (1, 3); and (3, 3). Higher order modes will produce more nodes and antinodes, result in three-dimensional standing waves in the water layer, characterized by strong gradients in the acoustic field in all directions, not only in the direction of the standing waves, but also in the lateral directions. As a consequence, the acoustic gradients result in stronger trapping forces in the lateral direction.

Figure 11:
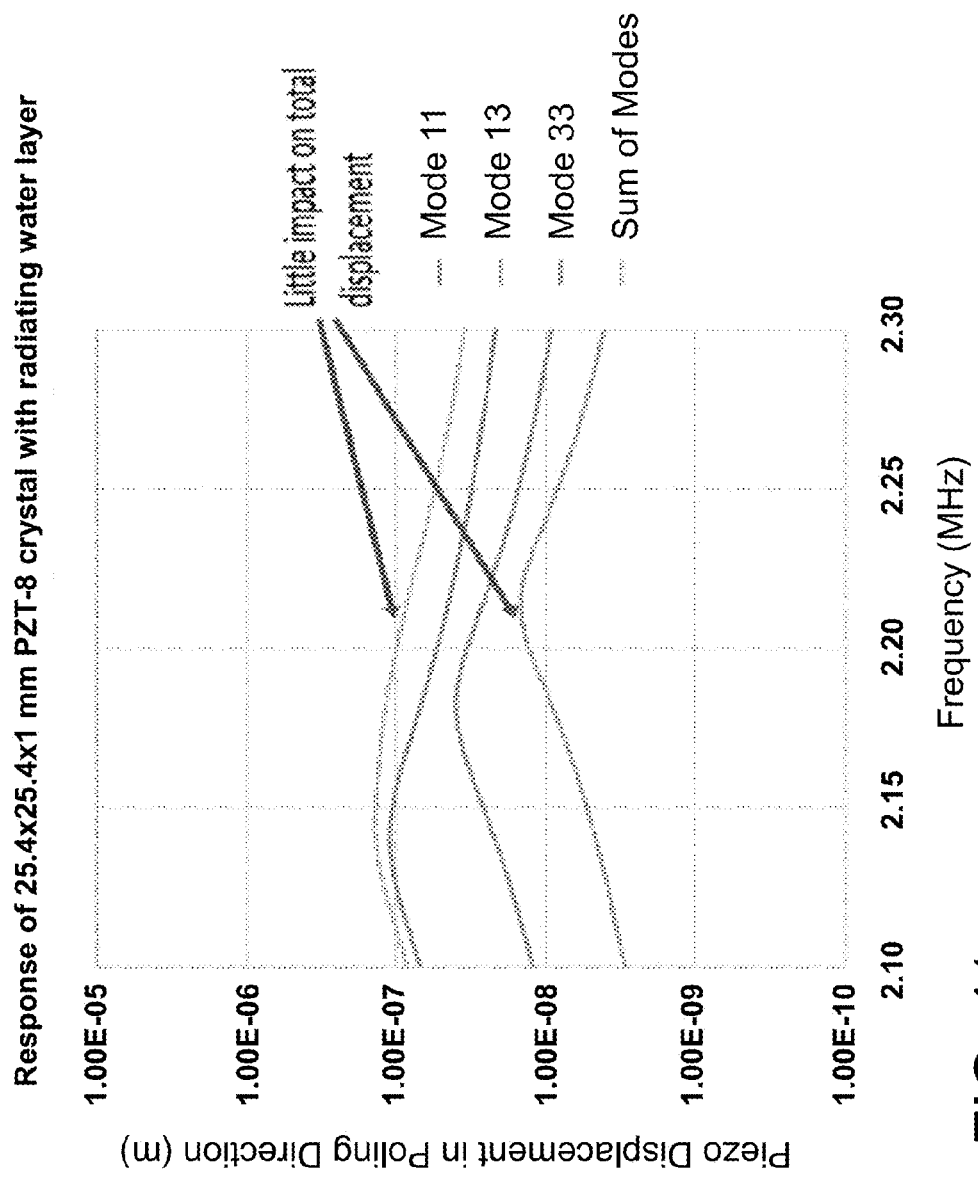
FIG. 11 presents analytical results for the displacement response of a 25.4×25.4×1 mm PZT-8 piezoelectric crystal with a radiating water layer.

FIG. 11 presents analytical results for the displacement response of a 25.4×25.4×1 mm PZT-8 piezoelectric crystal radiating into a semi-infinite water layer. The crystal was driven in three different (m, n) modes: Mode 11 (1, 1), Mode 13 (1, 3), and Mode 33 (3, 3). In FIG. 11, the uppermost line represents the sum of all three modes, the upper middle line represents Mode 11, the lower middle line represents Mode 13, and the lowermost line represents Mode 33. As can be seen in FIG. 11, there is little impact on the total displacement of the piezoelectric crystal in the poling direction. When the piezoelectric element radiates into a water layer, its displacement profile is mostly that of the fundamental mode. The displacement amplitude of the higher order modes are smaller across the entire frequency range of interest and thereby have minimal effect on the generation of the radiated acoustic wave. Note also that the resonance frequencies of the higher order modes increase with mode number.

Figure 12:
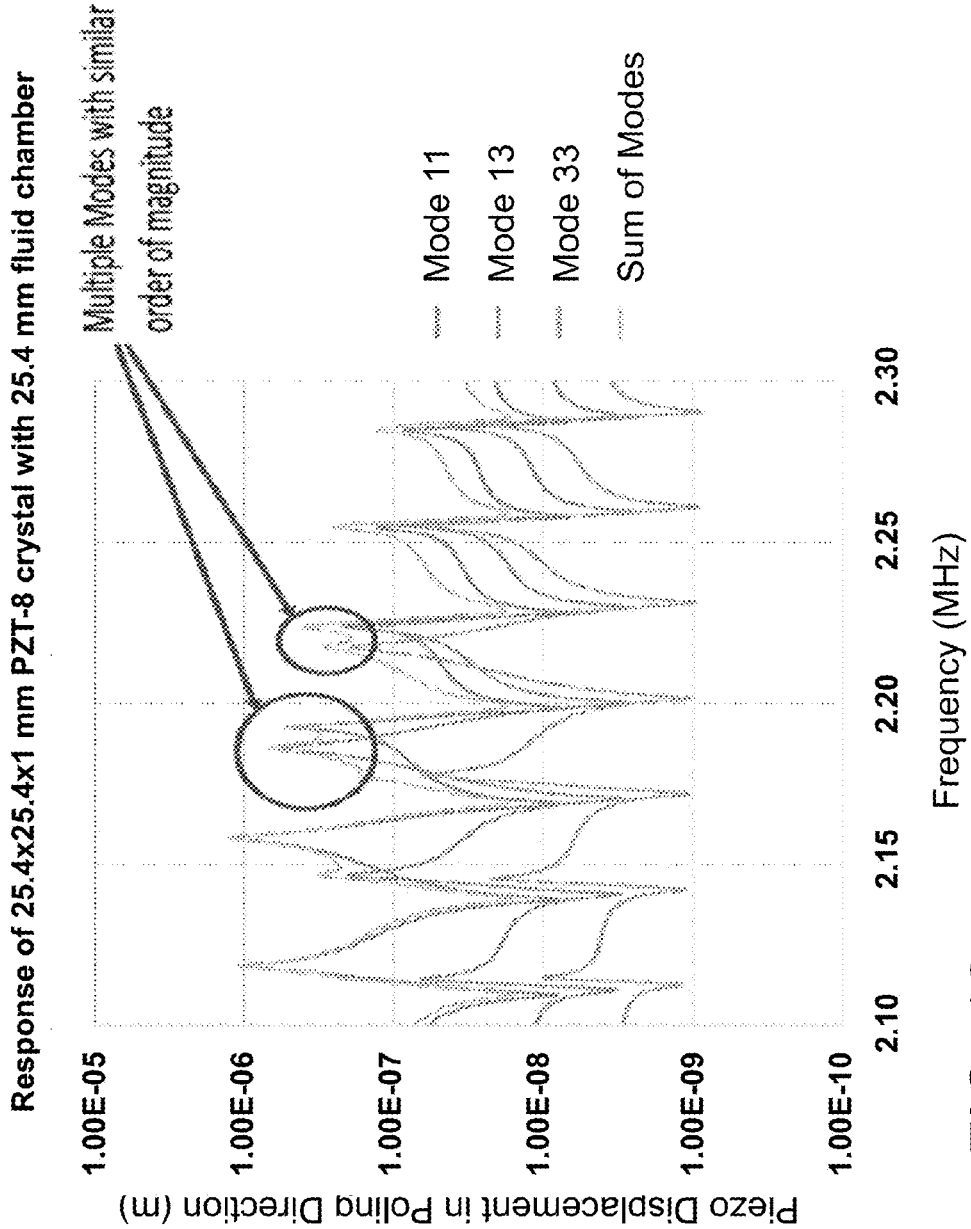
FIG. 12 presents analytical results for the displacement response of a 25.4×25.4×1 mm PZT-8 piezoelectric crystal with a 25.4 mm fluid chamber terminated by an acoustic reflector.

FIG. 12 presents analytical results for the displacement response of a 25.4×25.4×1 mm PZT-8 piezoelectric crystal with a 25.4 mm fluid chamber terminated by a rigid acoustic reflector. Again, the crystal was driven in three different (m, n) modes: Mode 11 (1, 1), Mode 13 (1, 3), and Mode 33 (3, 3). In FIG. 12, the uppermost line represents the sum of all three modes, the upper middle line represents Mode 11, lower middle line represents Mode 13, and the lowermost line represents Mode 33. As can be seen by comparing FIG. 12 with FIG. 11, in FIG. 12 there are multiple modes with similar orders of magnitude of displacement of the piezoelectric crystal in the poling direction. Put another way, the fundamental mode (1, 1) is no longer dominant at all frequencies. For some frequencies of excitation, the (1, 3) mode is dominant, while the (3, 3) mode is dominant for another frequency. For other frequencies, the strength of several modes are similar, and therefore all contribute to the overall displacement profile, which is then a superposition of each of the modes. It should be noted that the peaks in displacement of the three modes overlap each other at roughly equivalent frequencies in the region of higher frequencies. The peaks in each mode are roughly within 0.005 megahertz (MHz) of each other.

Figure 13:
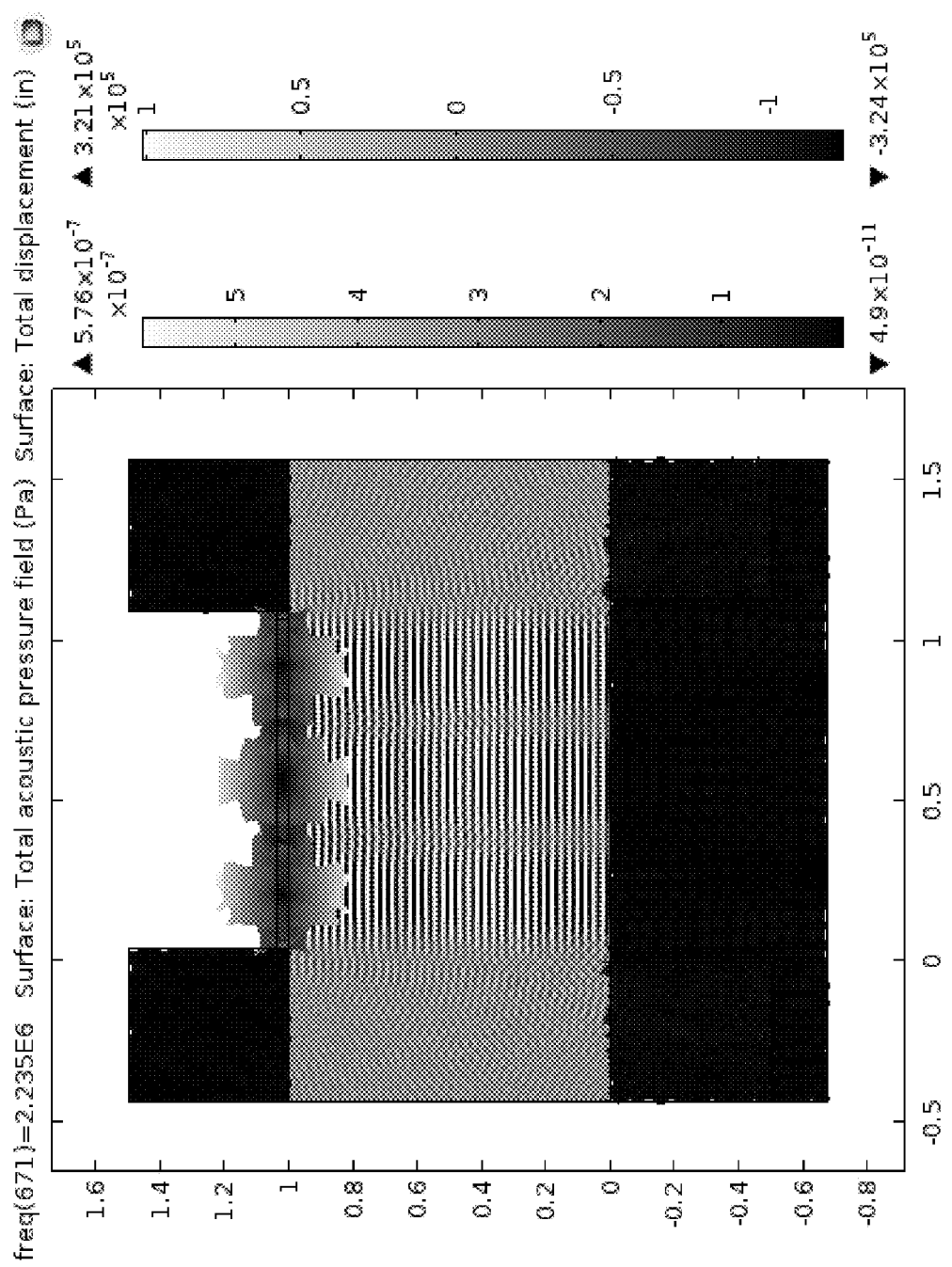
FIG. 13 presents a two-dimensional COMSOL numerical model of the piezoelectric equations according to the present disclosure.

Based on these analytical results, a numerical model was developed using the piezoelectric equations described above. In FIG. 13, this numerical model is represented in a two-dimensional COMSOL model in which the piezoelectric crystal(s) were operated at a frequency of 2.235 MHz. In FIG. 13, the y-axis represents the height of the system in inches and the x-axis represents the width of the system in inches. The two labels of the graph represent total displacement of the piezoelectric crystal in inches (right most label), and the inner label represents the acoustic potential (U). As can be seen in FIG. 13, the generation of a multi-dimensional acoustic standing wave creates multiple lines of acoustic potential minima.

Figure 14:
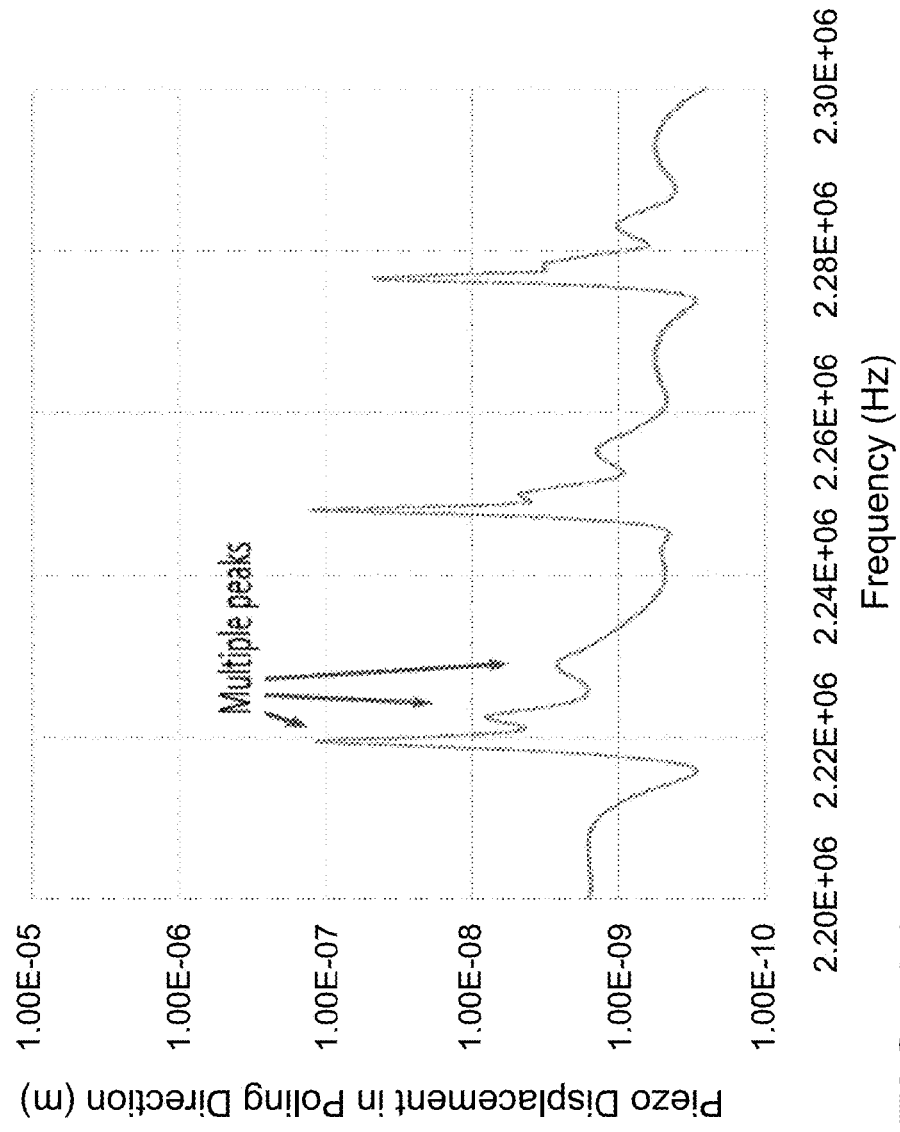
FIG. 14 presents numerical results for the displacement response of a 25.4×25.4×1 mm PZT-8 piezoelectric crystal with a 25.4 mm fluid chamber terminated by an acoustic reflector.
Figure 15:
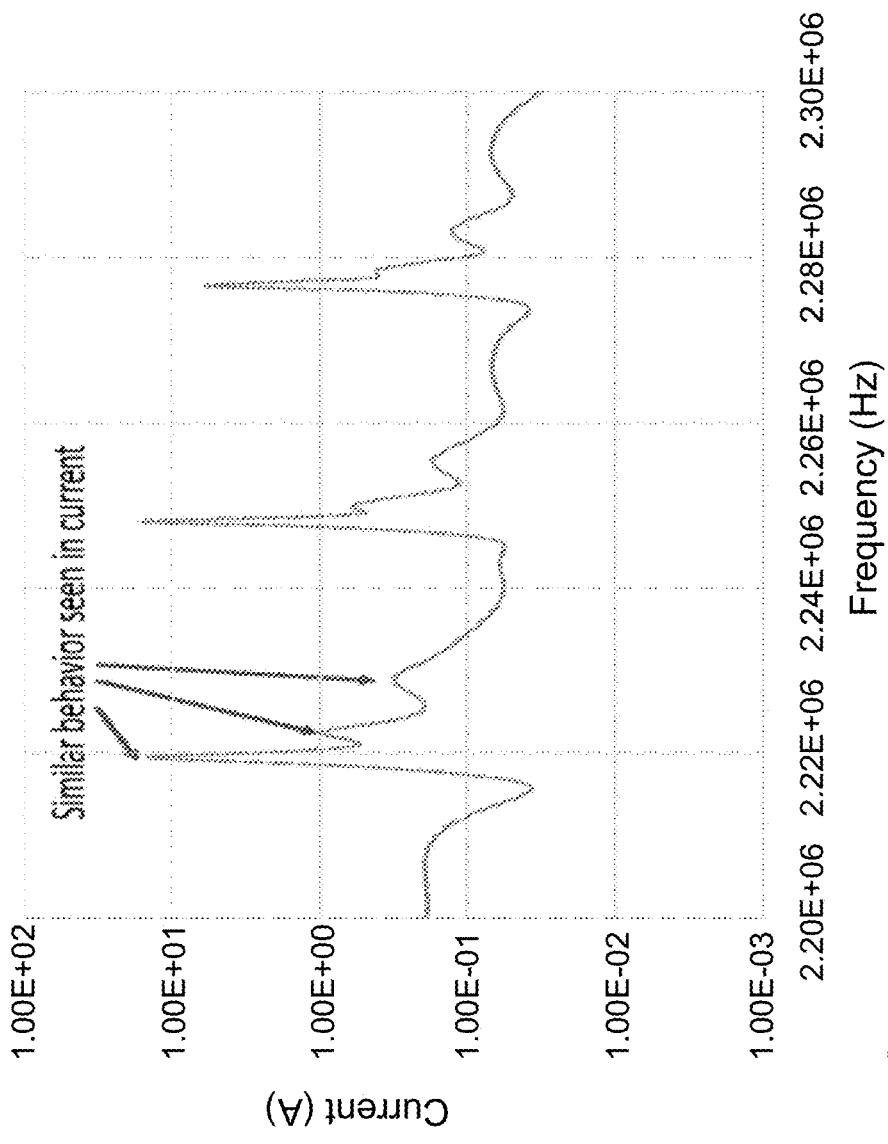
FIG. 15 presents numerical results for the current response of a 25.4×25.4×1 mm PZT-8 piezoelectric crystal with a 25.4 mm fluid chamber terminated by an acoustic reflector.

FIG. 14 and FIG. 15 present these numerical results. More specifically, FIG. 14 presents numerical results for the displacement response of a 25.4×25.4×1 mm PZT-8 piezoelectric crystal with a 25.4 mm fluid chamber. As can be seen in FIG. 14, the displacement profile has multiple peaks across the range of operating frequencies. For a 25.4 mm fluid layer, the planar acoustic resonance frequency spacing is about 29 kHz. The additional peaks seen in FIG. 15 are indications of the action of the higher order modes, similar to the predictions of the theoretical model. FIG. 15 presents numerical results for the current response of a 25.4×25.4×1 mm PZT-8 piezoelectric crystal with a 25.4 mm fluid chamber. As can be seen by comparing FIG. 15 with FIG. 14, the current response shows similar behavior to the displacement response, insofar as the current response has multiple peaks across the range of operating frequencies.

Figure 16:
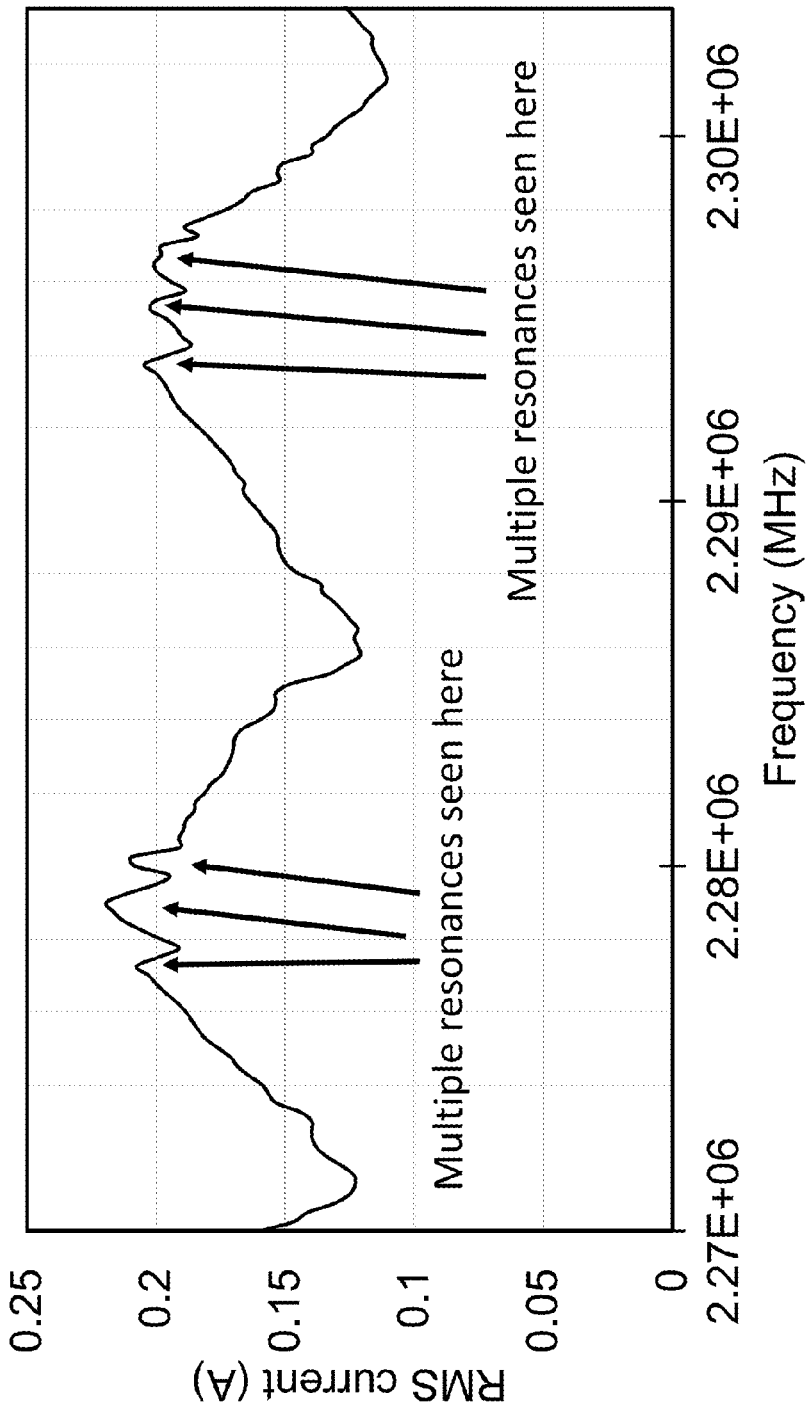
FIG. 16 presents experimental results for the current response of a 25.4×25.4×1 mm PZT-8 piezoelectric crystal operated with a 30 kHz frequency sweep with a 25.4 mm fluid chamber terminated by an acoustic reflector.

In embodiments, the voltage signal driving the transducer can have a sinusoidal, square, sawtooth, pulsed, or triangle waveform; and have a frequency of 500 kHz to 10 MHz. The voltage signal can be driven with pulse width modulation, which produces any desired waveform. The voltage signal can also have amplitude or frequency modulation start/stop capability to eliminate streaming. In one experimental setup shown in FIG. 16, a 30 kHz sweep was used, and the current response was plotted versus frequency, similar to FIG. 15. As seen in FIG. 16, multiple resonance peaks were found to exist, showing that the experimental results confirm both the theoretical and numerical results.

The transducers are used to create a pressure field that generates acoustic radiation forces of the same order of magnitude both orthogonal to the standing wave direction and in the standing wave direction. When the forces are roughly the same order of magnitude, particles of size 0.1 microns to 300 microns will be moved more effectively towards "trapping lines," so that the particles will not pass through the pressure field. Instead, the particles will remain within the acoustic chamber, from which they can advantageously be collected via specified outlets of the acoustophoretic device or otherwise recycled back to an associated bioreactor.

The acoustophoretic devices and methods described herein are useful for separating a second fluid or particulate from a host fluid. In this regard, the devices and methods of the present disclosure utilize higher order modal displacement of a piezoelectric element, with multiple modes having the same order of magnitude, which allows for stronger and more efficient trapping of the second fluid or particulate.

The present disclosure has been described with reference to exemplary embodiments. Modifications and alterations may occur to others upon reading and understanding the preceding detailed description. It is intended that the present disclosure be construed as including all such modifications and alterations insofar as they come within the scope of the appended claims or the equivalents thereof.

The invention claimed is:

1. A device for separating a second fluid or a particulate from a host fluid, comprising:
an acoustic chamber including at least one inlet and at least one outlet;
at least one ultrasonic transducer coupled to the acoustic chamber to permit generation of an acoustic wave therein, the at least one ultrasonic transducer including a piezoelectric material configured to be driven in a displacement profile that is a superposition of a combination of different modes that are the same order of magnitude to create a multi-dimensional acoustic standing wave in the acoustic chamber; and
a reflector across the acoustic chamber from the at least one ultrasonic transducer.

2. The device of claim 1, wherein the different modes have peaks within a frequency interval between resonance frequencies of planar standing waves.

3. The device of claim 1, wherein the combination of different modes is at least two of modes (1, 1); (1, 3); (1, 5); (3, 3); (3, 5); and (5, 5).

4. The device of claim 1, wherein the piezoelectric material is configured to vibrate to create an acoustic pressure profile in the acoustic chamber in a direction that is orthogonal to a direction of propagation of the acoustic standing wave, the pressure profile including multiple maxima and minima.

5. The device of claim 1, wherein the at least one ultrasonic transducer comprises:
a housing with a top end, a bottom end, and an interior volume; and
a piezoelectric element at the bottom end of the housing that includes an exposed exterior surface and an interior surface, the piezoelectric element being able to vibrate when driven by a voltage signal.

6. The device of claim 5, wherein a backing layer contacts the interior surface of the piezoelectric element, the backing layer being made of a substantially acoustically transparent material, and wherein (i) the substantially acoustically transparent material is balsa wood, cork, or foam; or (ii) wherein the substantially acoustically transparent material has a thickness of up to 1 inch, or (iii) wherein the substantially acoustically transparent material is in the form of a lattice.

7. The device of claim 5, wherein an exterior surface of the piezoelectric element is covered by a wear surface material with a thickness of a half wavelength or less, the wear surface material being a urethane, epoxy, or silicone coating.

8. The device of claim 5, wherein the piezoelectric element is free of a backing layer or a wear layer.

9. The device of claim 1, wherein the reflector includes a non-planar surface.

10. The device of claim 1, wherein the multi-dimensional acoustic standing wave is generated in the acoustic chamber normal to a direction of flow therethrough.

11. The device of claim 1, wherein the reflector is a piezoelectric acoustic transducer.

12. A device for separating a second fluid or a particulate from a host fluid, comprising:
an acoustic chamber including at least one inlet and at least one outlet;
at least one ultrasonic transducer coupled to the acoustic chamber to permit generation of an acoustic wave therein, the at least one ultrasonic transducer including a piezoelectric material configured to be driven at a frequency of excitation that excites multiple modes at the same time, to create a multi-dimensional acoustic standing wave in the acoustic chamber.

13. The device of claim 12, wherein the multiple modes are of the same order of magnitude.

14. The device of claim 12, wherein the multiple modes have peaks within a frequency interval between resonance frequencies of planar standing waves.

15. The device of claim 14, wherein the multiple modes have peaks within a 50% portion of a frequency interval between resonance frequencies of the planar standing waves.

16. The device of claim 12, wherein the multiple modes include at least two modes selected from the group consisting of modes (1, 1); (1, 3); (1, 5); (3, 3); (3, 5); and (5, 5).

17. The device of claim 12, further comprising a reflector located opposite from the at least one ultrasonic transducer.

18. A device for separating a second fluid or a particulate from a host fluid, comprising:
an acoustic chamber including at least one inlet and at least one outlet;
at least one ultrasonic transducer coupled to the acoustic chamber to permit generation of an acoustic wave therein, the at least one ultrasonic transducer including a piezoelectric material configured to be driven so that the piezoelectric material vibrates in higher order modes of the general formula (m, n), wherein m and n are independently 1 or greater, to create a multi-dimensional acoustic standing wave in the acoustic chamber; and a reflector located opposite to the at least one ultrasonic transducer.

19. The device of claim 18, wherein the higher order modes are of the same order of magnitude.

20. The device of claim 18, wherein the higher order modes include at least two modes selected from the group consisting of modes (3, 3); (3, 5); and (5, 5).

21. A device for separating a second fluid or a particulate from a host fluid, comprising:
an acoustic chamber including at least one inlet and at least one outlet;
at least one ultrasonic transducer coupled to the acoustic chamber to permit generation of an acoustic wave therein, the at least one ultrasonic transducer including a piezoelectric material configured to be driven in a displacement profile that is a superposition of a combination of different modes to create a multi-dimensional acoustic standing wave in the acoustic chamber;

where the multidimensional acoustic standing wave is the result of the perturbation of a PZT (Lead Zirconate Titanate) material having characteristics of a 33 orientation where the piezoelectric elements are characterized by independent $\lambda$ values, independent e values, and independent $\epsilon$ values such that, in a resonant cavity with an acoustic standing wave, the electrical boundary conditions are defined by the following equations:

$$\varphi(x, y, z = d_z) = \sum_{n,m} V_{n,m} \cos k_{xn} x \cos k_{ym} y$$

$$\phi(x,y,z=0)=0$$

where V is the voltage amplitude, n is the periodic index, and m is the periodic index for the (n,m) mode of interest; and
a reflector located across the acoustic chamber from the at least one ultrasonic transducer.

* * * * *